(12) United States Patent
Nachum et al.

(10) Patent No.: US 8,755,894 B2
(45) Date of Patent: *Jun. 17, 2014

(54) METHOD AND DEVICE FOR ENHANCED BLOOD FLOW

(75) Inventors: Zvi Nachum, Tiberias (IL); Yaakov B. Brezel, Jerusalem (IL); Shalom Lampert, Maalot (IL)

(73) Assignee: Empire Bio-Medical Devices Inc., Brooklyn, NY (US)

( * ) Notice: Subject to any disclaimer, the term of this patent is extended or adjusted under 35 U.S.C. 154(b) by 91 days.

This patent is subject to a terminal disclaimer.

(21) Appl. No.: 13/153,493

(22) Filed: Jun. 6, 2011

(65) Prior Publication Data

US 2011/0288602 A1     Nov. 24, 2011

Related U.S. Application Data

(63) Continuation-in-part of application No. 11/438,070, filed on May 22, 2006, now Pat. No. 7,991,476, and a continuation-in-part of application No. 12/965,883, filed on Dec. 12, 2010, now abandoned, which is a continuation-in-part of application No. PCT/IL2009/000584, filed on Jun. 14, 2009, and a continuation-in-part of application No. 12/853,491, filed on Aug. 10, 2010, which is a continuation-in-part of application No. PCT/IL2009/000145, filed on Feb. 8, 2009.

(60) Provisional application No. 61/027,464, filed on Feb. 10, 2008.

(51) Int. Cl.
*A61N 1/00* (2006.01)

(52) U.S. Cl.
USPC .......................................................... 607/48

(58) Field of Classification Search
None
See application file for complete search history.

(56) References Cited

U.S. PATENT DOCUMENTS

| | | | |
|---|---|---|---|
| 7,991,476 B2 * | 8/2011 | Nachum | 607/48 |
| 2004/0030270 A1 * | 2/2004 | Johnson | 601/15 |
| 2005/0131489 A1 * | 6/2005 | Gardon-Mollard | 607/49 |
| 2007/0270917 A1 * | 11/2007 | Nachum | 607/48 |
| 2009/0124944 A1 * | 5/2009 | Ravikumar | 601/149 |

* cited by examiner

Primary Examiner — Mark W Bockelman

(57) ABSTRACT

A non-invasive method comprising positioning a first electrode on a lower end of a lower leg, a second electrode on the lower leg, and a third electrode on an upper end of the lower leg, whereby the first and third electrodes are disposed on opposite ends of the lower leg, and the second electrode and one of the first and third electrodes are disposed on a same end of the lower leg; effecting a sequence of muscular contractions of the lower leg by (i) applying a first electrical impulse between the electrodes on the same end of the lower leg to induce a first muscular contraction and (ii) applying at least a second electrical impulse between the first and third electrodes to induce a longitudinal muscular contraction; and repeating operations (i) and (ii), to repeatedly induce the contractions, to effect the increased flow of blood.

10 Claims, 17 Drawing Sheets

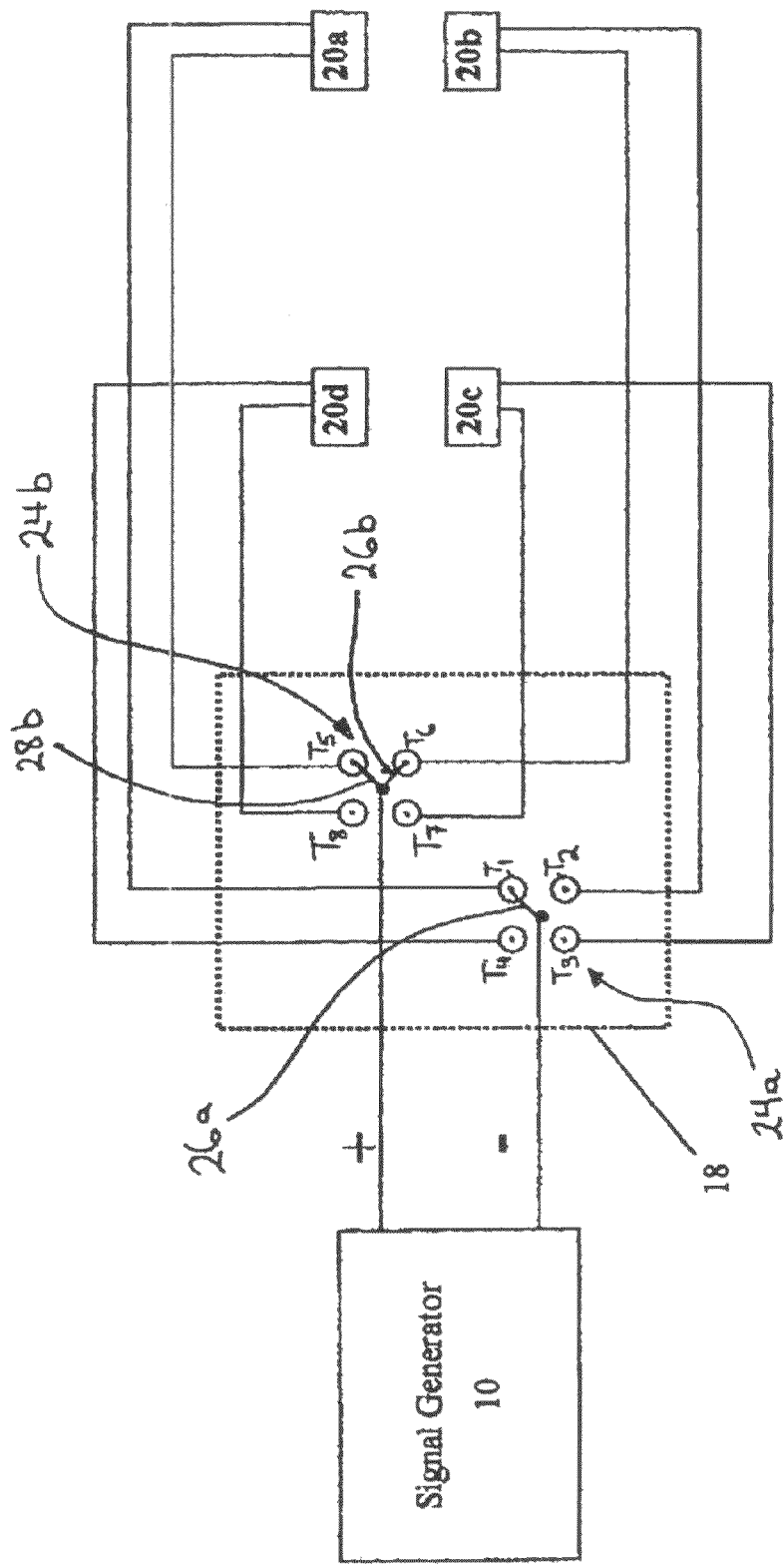

METHOD AND DEVICE FOR ENHANCED BLOOD FLOW

This patent application is a continuation-in-part of: U.S. patent application Ser. No. 11/438,070 filed on May 22, 2006; U.S. patent application Ser. No. 12/965,883 filed on Dec. 12, 2010, which is a continuation-in-part of PCT/IL2009/000584 filed on Jun. 14, 2009; and U.S. patent application Ser. No. 12/853,491 filed on Aug. 8, 2010, which is a continuation-in-part of PCT/IL2009/000145 filed on Feb. 8, 2009 and which claims priority to U.S. Provisional Patent Application Ser. No. 61/027,464, filed on Feb. 10, 2008, all of which are all hereby incorporated in their entirety by reference.

FIELD AND BACKGROUND OF THE INVENTION

The present invention relates to a method and device for promoting a localized change in the flow of blood through a blood vessel, and more particularly, to a non-invasive method and device for promoting a localized change in the flow of blood by electrically-induced contractual movement of muscular tissue.

Current treatments for improving blood circulation and alleviating neural and muscle pain include manual, electrical, and mechanical methods. Manual treatment as practiced in physiotherapy requires massaging to be administered by qualified personnel. The efficacy of this personnel-intensive art varies with the experience and technique of the individual massage therapist, and therefore cannot be prescribed in an adequately standardized form. More importantly, the improvement in blood circulation is also of an extremely limited magnitude.

Electrical Muscle Stimulation (EMS) has seen widespread use in many applications. The Food and Drug Administration (Section 355.200 Electrical Muscle Stimulators, CPG 7124.26) maintains that EMS devices are recognized in the health care community as being effective for muscle reeducation, relief of muscle spasm, increasing range of motion, disuse atrophy therapy, increased local blood circulation, and immediate post-surgical stimulation of calf muscles to prevent venous thrombosis. It must be emphasized, however, that the stimulation provided by EMS is very similar to the stimulation achieved by therapeutic massage. Any increase in blood circulation is so modest that it is often undetectable using conventional flow-measuring equipment. EMS is a random excitation of a local tissue area. Hence, EMS methods, like therapeutic massage, hot-water treatments, etc. are incapable of providing a major increase in the localized flow of blood. Moreover, because the excitation is random, EMS methods are fundamentally incapable of providing a decrease in the localized flow of blood.

Also known is a sequential pneumatic device for the reduction of an edema. The device consists of several overlapping compartments contained in a sleeve assembly. The compartments are inflated in a sequential fashion, from a distal end disposed adjacent to the edema, to a proximal end, such that the edema is pressed in the proximal direction. Each compartment is filled with air by a pump. The cycle starts with the filling of the distal compartment, and subsequently the remaining compartments are filled until all compartments are full. After a deflation period, the cycle is repeated.

This and other treatments employ electromechanical installations in which electric motors and reciprocating mechanisms create uncomfortable noise and vibration. These treatments are of further disadvantage in that they require various device elements to be contacted with the skin. These elements generally cause discomfort to the patient, and require changing and cleaning after each use in order to ensure good sanitary conditions.

U.S. Pat. No. 5,674,262 to Tumey teaches a device and method for stimulating blood flow velocity in a leg, in an effective and relatively painless manner, so as to prevent deep vein thrombosis. The device includes a mechanical compressing apparatus for compressing a foot so as to drive a substantial amount of blood from veins of the foot into blood vessels of the leg, and a second apparatus, operatively associated with the compressing apparatus, for electrically stimulating leg muscles as the driven blood from the foot passes therethrough. The resultant muscle activity enhances the blood flow velocity to the point where endothelial derived relaxing factor (EDRF) is produced, which dilates the blood vessel and enables a higher flowrate of blood to be delivered.

Significantly, U.S. Pat. No. 5,674,262 teaches that electrical stimulation, in and of itself, is not efficacious for stimulating blood flow, and does not bring about EDRF production.

U.S. patent application Ser. No. 10/451,334 to Nachum teaches treatment methods for promoting a localized increase in the flow of blood through a blood vessel in an area of the body. In these treatment methods, electrical impulses from the signal generator are applied to body tissue, by means of electrodes, so as to subject the adjacent muscular tissue to at least one voltage differential, thereby inducing a repeated, contracting movement of muscular tissue associated with the local blood vessels. This movement of muscular tissue produces a localized increase in the flow of blood through these blood vessels.

In preferred embodiments, treatment is effected by placing the electrodes at opposite ends of the limb segment, and applying the electrical impulses so as to establish a voltage differential between the electrodes. The voltage differential is made up of two wave forms propagated in opposite directions between the electrodes.

It would be highly advantageous to have, an improved, efficacious device and method for more efficiently promoting, upon demand, the localized circulation of blood through blood vessels. It would be of further advantage if the device and method would be simple, robust, non-invasive, repeatable, and adjustable to the individual needs of the patient.

SUMMARY OF THE INVENTION

According to the teachings of the present invention there is provided a non-invasive method for promoting a localized change in a flow of blood through a blood vessel in a limb segment of a body by a series of electrically stimulated contractions of muscle tissue in the limb segment, the method including the steps of: (a) providing a device including: (i) a plurality of electrodes including at least a first electrode, a second electrode, and a third electrode, each of the electrodes for operatively contacting the limb segment of the body; (ii) a signal generator, operatively connected to each electrode, for producing a series of electrical impulses to the limb segment via the plurality of electrodes, the signal generator for connecting to a power supply, and (iii) a control unit, associated with the signal generator, for controlling the signal generator so as to produce the series of electrical stimulation impulses, the impulses being of pre-determined voltage differential, form, and duration; (b) positioning the plurality of electrodes on the limb segment; (c) applying at least one of the electrical impulses so as to induce a substantially radial contraction of a first portion of the muscular tissue in the limb segment; and (d) applying at least one of the electrical impulses so as to induce a substantially longitudinal contraction of a second portion of the muscular tissue in the limb segment, such that the muscular tissue acts upon the blood vessel to produce the localized change in the flow of blood through the limb segment.

According to further features in the described preferred embodiments, the device further includes: (iv) a switching mechanism, responsive to the control unit, designed and configured for switching electrical connections between the signal generator and each of the electrodes, according to a pre-determined sequence.

According to further features in the described preferred embodiments, the substantially radial contraction is induced by providing at least a first voltage differential between the first electrode and the second electrode, and wherein the substantially longitudinal contraction is induced by providing at least a second voltage differential between the second electrode and the third electrode.

According to further features in the described preferred embodiments, the method further includes the step of: switching electrical connections, by means of the switching mechanism, between the signal generator and each of the electrodes, so as to deliver the series of electrical stimulation impulses.

According to further features in the described preferred embodiments, the localized change is an increase in the flow of blood through the blood vessel.

According to further features in the described preferred embodiments, the localized change is a decrease in the flow of blood through the blood vessel.

According to further features in the described preferred embodiments, the series of electrical impulses includes a plurality of voltage differential peaks, each of the peaks having a duration of 80-1200 microseconds.

According to further features in the described preferred embodiments, the series of electrical impulses includes a plurality of voltage differential peaks, each of the peaks having a duration of 100-600 microseconds.

According to further features in the described preferred embodiments, the device further includes: (iv) a switching mechanism, responsive to the control unit, designed and configured for switching electrical connections between the signal generator and each of the electrodes, according to a pre-determined sequence, so as to deliver the series of electrical stimulation impulses by providing at least a first voltage differential between the first electrode and the second electrode, a second voltage differential between the second electrode and the third electrode, and a third voltage differential between the third electrode and another electrode of the plurality of electrodes.

According to further features in the described preferred embodiments, steps (c) and (d) are performed such that the longitudinal contraction is induced while the first portion of the muscular tissue remains at least partially contracted.

According to still further features in the described preferred embodiments, the radial contraction is effected upstream of the longitudinal contraction.

According to still further features in the described preferred embodiments, the method further includes the step of: (e) applying at least one of the electrical impulses so as to induce a second substantially radial contraction of a third portion of the muscular tissue in the limb segment.

According to still further features in the described preferred embodiments, the second radial contraction is effected downstream of the longitudinal contraction.

According to still further features in the described preferred embodiments, the "another electrode", referred to hereinabove, is a fourth electrode of the plurality of electrodes.

According to another aspect of the present invention there is provided a non-invasive device for promoting a localized increase or decrease in a flow of blood through a blood vessel in a limb segment of a body, the device including: (a) a plurality of electrodes including at least a first electrode, a second electrode, and a third electrode, each of the electrodes for operatively contacting the limb segment of the body; (b) a signal generator, operatively connected to each electrode, for providing a series of electrical impulses to the limb segment via the plurality of electrodes, the signal generator for connecting to a power supply; (c) a control unit, associated with the signal generator, for controlling the signal generator so as to produce the series of electrical stimulation impulses, the impulses being of pre-determined voltage differential, form, and duration, and (d) a switching mechanism designed and configured for switching electrical connections between the signal generator and each of the electrodes, according to a pre-determined sequence, so as to provide a first voltage differential between the first electrode and the second electrode, a second voltage differential between the second electrode and the third electrode, and a third voltage differential between the third electrode and another electrode of the plurality of electrodes.

According to further features in the described preferred embodiments, the control unit is designed and configured such that when the plurality of electrodes is disposed on the limb segment, the first, second and third voltage differentials promote a localized change in the flow of blood through the blood vessel.

According to still further features in the described preferred embodiments, the switching mechanism is responsive to the control unit.

According to still further features in the described preferred embodiments, the control unit and the switching mechanism are configured such that a frequency of the series of electrical stimulation impulses delivered to the electrodes is 1-30 periods per minute, and more preferably, 5-20 periods per minute.

According to still further features in the described preferred embodiments, the signal generator and the control unit are designed and configured such that the series of electrical impulses has a cycle frequency in the range of 0.5-20 Hz, and more preferably, in the range of 6-15 Hz.

According to still further features in the described preferred embodiments, the control unit is designed and configured such that when the plurality of electrodes is disposed on the limb segment, the first, second and third voltage differentials induce at least one substantially radial contraction of a first portion of the muscular tissue in the limb segment, at least partially followed by substantially longitudinal contraction of a second portion of the muscular tissue in the limb segment, so as to effect the localized change in the flow of blood through the blood vessel.

According to yet another aspect of the present invention there is provided a non-invasive device for promoting a localized change in a flow of blood through a blood vessel in a limb segment of a body, the device including: (a) a plurality of electrodes including at least a first electrode, a second electrode, and a third electrode, each of the electrodes for operatively contacting the limb segment of the body; (b) a signal generator, operatively connected to each electrode, for providing a series of electrical impulses to the limb segment via the plurality of electrodes, the signal generator for connecting to a power supply; (c) a control unit, associated with the signal generator, for controlling the signal generator to produce the series of electrical stimulation impulses, the impulses being of pre-determined voltage differential, form, and duration, wherein the control unit is designed and configured whereby, when the plurality of electrodes is disposed on the limb segment, the series of electrical stimulation impulses induces at least one substantially radial contraction of a first portion of the muscular tissue in the limb segment, the radial contraction at least partially followed by a substantially longitudinal contraction of a second portion of the muscular tissue in the limb segment, so as to effect the localized change in the flow of blood through the limb segment.

According to yet another aspect of the present invention there is provided a non-invasive method for promoting a localized increase in a flow of blood through a blood vessel in a limb segment on a lower leg of a body of a subject by a series of electrically stimulated contractions of muscle tissue in the limb segment, the method including the steps of: (a) providing a device including: (i) at least a first electrode, a second electrode, and a third electrode, each of the electrodes adapted to operatively contact the limb segment; (ii) a signal generator, operatively connected to each electrode, adapted to produce a series of electrical impulses to the limb segment via the plurality of electrodes, the signal generator connecting to a power supply, and (iii) a control unit, associated with the signal generator, adapted to control the signal generator to produce the series of electrical impulses, the impulses being of pre-determined voltage differential, form, and duration; (b) positioning the plurality of electrodes on the limb segment, wherein the first electrode is positioned on a lower end of the lower leg, the second electrode is positioned on the lower leg, and the third electrode is positioned on an upper end of the lower leg, whereby the first electrode and the third electrode are disposed on opposite ends of the lower leg, and the second electrode and one of the first and third electrodes are disposed on a same end of the lower leg; (c) effecting a sequence of muscular contractions of the lower leg, by operations including: (i) applying at least a first electrical impulse of the electrical impulses between the electrodes on the same end of the lower leg to induce a first muscular contraction of a first portion of the tissue in the lower leg; and (ii) applying at least a second electrical impulse of the electrical impulses between the first and third electrodes to induce a longitudinal muscular contraction of a second portion of the muscular tissue in the lower leg; and (d) repeating operations (i) and (ii), to repeatedly induce at least the first muscular contraction and the longitudinal muscular contraction, to effect the localized increase in the flow of blood.

According to still further features in the described preferred embodiments, the frequency of a sequence including steps (c) and (d) is 1-60 periods per minute (ppm), 2-60 ppm, 3-60 ppm, or 5-30 ppm.

According to still further features in the described preferred embodiments, the device further includes: a compression unit, adapted to at least partially envelope the limb segment, said electrodes physically attached to the compression unit and at least partially disposed thereunder, the compression unit having an inside face adapted to deliver, to a surface of the limb segment, a superatmospheric pressure that is substantially constant over time, the pressure equaling at least 5 mmHg, at least 8 mmHg, at least 12 mmHg, or at least 16 mmHg.

According to still further features in the described preferred embodiments, the method further includes the steps of positioning the compression unit on the limb segment, to at least partially cover the portions of the tissue, and exerting, on a surface of the limb segment, by means of the compression unit, a superatmospheric pressure that is substantially constant over time, the pressure equaling at least 5 mmHg, at least 8 mmHg, at least 12 mmHg, or at least 16 mmHg.

According to still further features in the described preferred embodiments, the plurality of electrodes includes a fourth electrode, preferably positioned on an upper end of the lower leg.

According to still further features in the described preferred embodiments, the sequence includes a muscular contraction of a third portion of the tissue in the lower leg, the contraction of the third portion of the tissue effected by applying at least one of the electrical impulses between the third electrode and the fourth electrode, positioned on an upper end of the lower leg.

According to still further features in the described preferred embodiments, the repeating sequence of muscular contractions includes a second longitudinal contraction of a third portion of the tissue in the lower leg, the second longitudinal contraction of the third portion of the tissue effected by applying at least one of the electrical impulses between the fourth electrode and at least one electrode disposed on the lower end of the lower leg.

According to still further features in the described preferred embodiments, the repeating sequence of muscular contractions includes a second longitudinal contraction of a fourth portion of the tissue in the lower leg, the second longitudinal contraction of the fourth portion of the tissue effected by applying at least one of the electrical impulses between the fourth electrode and at least one electrode disposed on the lower end of the lower leg.

According to still further features in the described preferred embodiments, the device further includes a wound treatment assembly including a wound cover adapted to cover an area above a wound on the body, a sealing arrangement, associated with the cover, adapted to contact and at least partially seal a volume beneath the cover from an ambient environment, and a vacuum mechanism fluidly communicating with the volume, and adapted to produce a sub-atmospheric pressure between about 0.01 and 0.95 bar, absolute, within the volume; and a control unit, adapted to connect to a power supply and operatively connected to the wound treatment assembly and further adapted to control an operation of the treatment assembly.

According to still further features in the described preferred embodiments, the method further includes the steps of disposing the wound cover over the wound; contacting the sealing arrangement with skin surrounding the wound; and activating the vacuum mechanism to produce the sub-atmospheric pressure within the volume.

According to still further features in the described preferred embodiments, the method further includes the steps of providing the control unit with at least one of an ankle-brachial index (ABI) and an ankle blood pressure of the desired limb of the subject, and responsive to at least one of the ABI and the ankle blood pressure of the desired limb, controlling the apparatus, using the control unit, to treat the subject.

According to still further features in the described preferred embodiments, when at least one of the ABI and the ankle blood pressure is below a pre-determined value, the control unit is configured to perform at least one safety operation.

According to still further features in the described preferred embodiments, the method is effected on a subject having an ankle-brachial index (ABI) below 0.7.

According to still further features in the described preferred embodiments, the electrical impulses of the series of electrical impulses are time-distinct impulses.

According to still further features in the described preferred embodiments, at least the first electrical impulse is applied in a radial direction with respect to the lower leg.

According to still further features in the described preferred embodiments, the first electrode is positioned above an ankle of the leg.

According to still further features in the described preferred embodiments, the lower leg has a particular length, and the electrodes are positioned at opposite ends of the lower leg, whereby the longitudinal contraction is effected over substantially the particular length of the lower leg.

According to still further features in the described preferred embodiments, the sub-atmospheric pressure within the volume is between 0.03 bar and 0.3 bar absolute, or between 0.05 and 0.25 bar absolute.

According to still further features in the described preferred embodiments, the muscular contraction of the first portion of the tissue is effected upstream of the longitudinal contraction.

According to still further features in the described preferred embodiments, the muscular contraction of the third portion of the tissue in the lower leg is effected downstream of the longitudinal contraction.

According to still further features in the described preferred embodiments, the muscular contraction of the first portion of the tissue is effected downstream of the longitudinal contraction.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 3 is a diagram showing an exemplary switching arrangement for the switching mechanism of the inventive device, and the electrical connections between the switching mechanism, the signal generator, and the surface electrodes;

DESCRIPTION OF THE PREFERRED EMBODIMENTS

Figure 1:
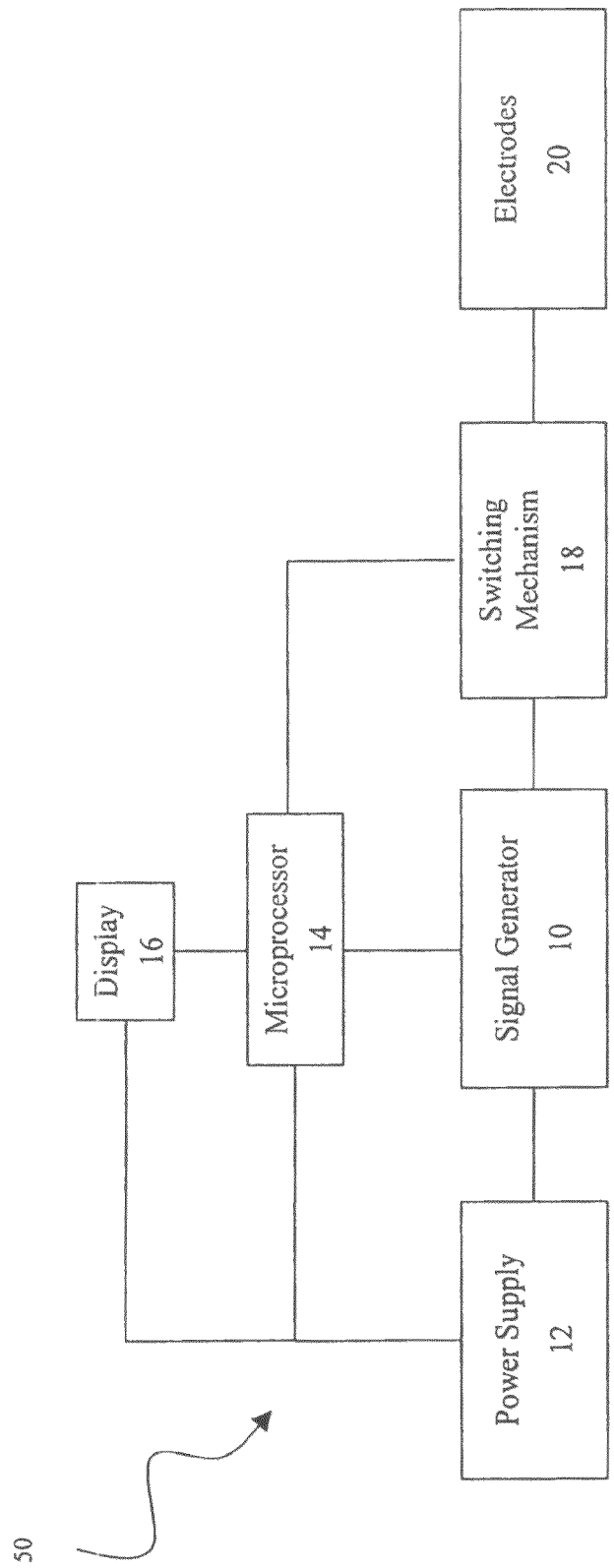
FIG. 1 is a block diagram that conceptually shows the main components of the device of the present invention.

According to the teachings of the present invention there is provided a method and device for externally promoting a localized increase in a flow of blood through a blood vessel in a particular area of the body.

Typically, this repeated contractual movement of voluntary muscular tissue can be harnessed to drive the oxygenated blood through the arteries to a limb extremity, and subsequently, to drive the oxygen-depleted blood back towards the heart, the net result being an increase in the supply of blood to the limb extremity.

Alternatively, the sequence of the repeated contractual movement of muscular tissue can be reversed, such that the flow of blood to a given area is reduced.

The principles and operation of this process according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

Referring now to the drawings, FIG. 1 is a block diagram showing the components of a stimulation device 50 according to the present invention. Signal generator 10 is operatively connected to a power supply 12. Also connected to power supply 12, are control unit or microprocessor 14 and display 16. Signal generator 10 can also be integral with microprocessor 14. Signal generator 10 is also operatively connected to a plurality of electrodes 20 via switching mechanism 18. Control unit 14 controls signal generator 10 so as to produce a series of electrical stimulation impulses. These impulses are delivered to electrodes 20 positioned on a limb segment of the patient, as will be explained in further detail hereinbelow. Switching mechanism 18 determines to which pair of electrodes the stimulation impulses will be delivered. Switching mechanism 18 can also be configured as a distributing mechanism that simultaneously distributes a positive or negative signal to two or more electrodes.

Thus, as used herein in the specification and in the claims section that follows, the term "switching mechanism" and the like, is meant to include a distributing mechanism that concurrently distributes a positive signal to two or more electrodes, or a negative signal to two or more electrodes.

Switching mechanism 18 can be a mechanical switching system, an electromechanical relay mechanism, or preferably, an electrical/electronic switching system controlled by control unit 14. A solid state relay having a photo-sensitive metal oxide semiconductor effect transistor (MOSFET) device with an LED to actuate the device is one presently preferred embodiment for switching mechanism 18.

Display 16, which is responsive to control unit 14, is advantageously configured to display information such as signal frequency, pulse width, period, and voltage.

Figure 2A:
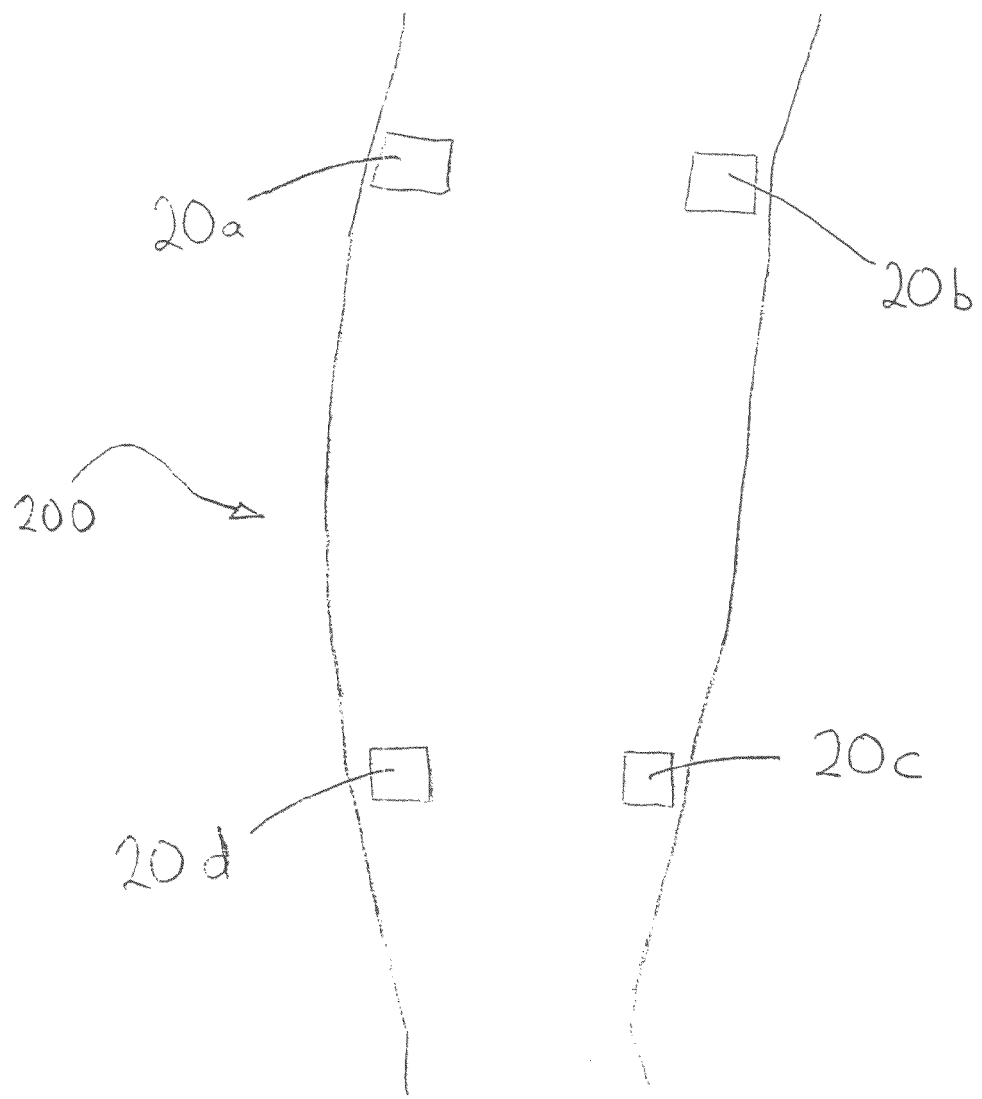
FIG. 2A provides a schematic illustration of a section of a lower leg, to which are affixed two electrode pairs, according to the present invention.
Figure 2B:
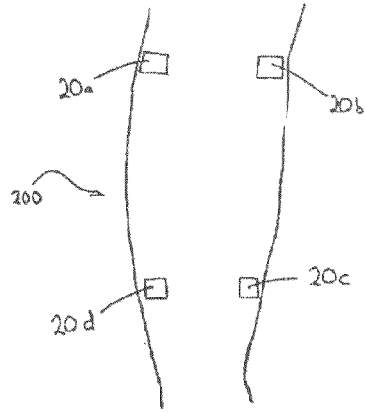
FIGS. 2B-2E is a schematic representation of the inventive contraction timing sequence provided by the control unit, by means of the switching mechanism, according to the present invention.
Figure 2C:
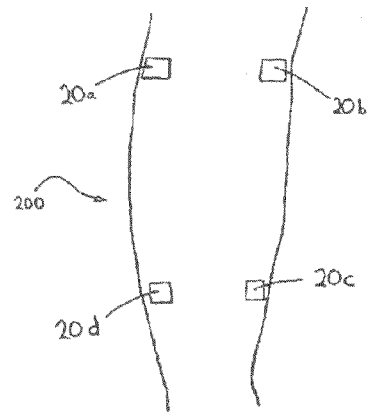

FIG. 2A provides a schematic illustration of a section of a limb segment such as lower leg 200, to which are affixed electrodes 20a-d, according to the present invention. A first pair of electrodes 20a-b is affixed at an upper end of lower leg 200 and a second pair of electrodes 20c-d is affixed at the opposite end of lower leg 200. Electrodes 20a-d are preferably positioned near the ends of the muscles of lower leg 200. Electrodes 20a-d are operatively connected to stimulation device 50 via switching mechanism 18, as shown in FIG. 1.

By applying a suitable voltage differential and current to electrodes 20a-d, muscular tissue in lower leg 200 contracts, thereby impinging upon the local blood vessels. It has been discovered by the inventor that with the proper electrical impulses and contraction positioning (constriction points), and timing sequence, the device of the present invention can be utilized to appreciably, measurably, and repeatably enhance the flow of blood through the limb segment.

The inventive contraction timing sequence will now be described, by way of example, with reference to FIGS. 1 and 2A, and in particular, with reference to FIG. 2B-2E. In step (I), shown schematically in FIG. 2B, switching mechanism 18 delivers a voltage differential from signal generator 10 (not shown) to first pair of electrodes 20a-b disposed at an upper end of lower leg 200. The resulting muscular contraction is substantially a radial muscular contraction 40 between electrodes 20a-b. In step (II), shown schematically in FIG. 2C, switching mechanism 18 delivers a voltage differential from signal generator 10 to an electrode from first pair of electrodes 20a-b and to an electrode from second pair of electrodes 20c-d disposed at a lower end of lower leg 200. By way of example, switching mechanism 18 delivers a positive voltage to electrode 20b and a negative voltage to electrode 20c. The resulting muscular contraction is substantially a longitudinal muscular contraction 42 along the length of lower leg 200.

Figure 2D:
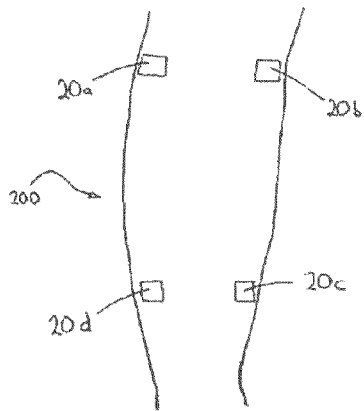

In step (III), shown schematically in FIG. 2D, switching mechanism 18 delivers a voltage differential from signal generator 10 to second pair of electrodes 20c-d. The resulting muscular contraction is substantially a radial muscular contraction 44 between electrodes 20c-d at or towards a lower end of lower leg 200. By way of example, switching mechanism 18 delivers a positive voltage to electrode 20c and a negative voltage to electrode 20d.

Figure 2E:
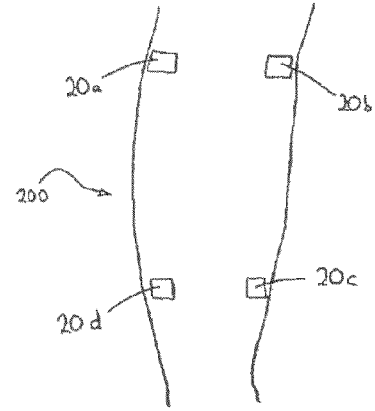

Step (IV), shown schematically in FIG. 2E, completes the cycle: switching mechanism 18 delivers a voltage differential from signal generator 10 to an electrode from first pair of electrodes 20a-b and to an electrode from second pair of electrodes 20c-d, so as to effect a substantially longitudinal muscular contraction 46 along the length of lower leg 200. By way of example, switching mechanism 18 delivers a positive voltage to electrode 20d and a negative voltage to electrode 20a.

It must be emphasized that the various known electrical stimulation devices for promoting a localized increase in the flow of blood are designed, configured, and operated so as to effect, solely, a substantially longitudinal muscular contraction along the length of the lower leg. However, effecting both radial muscular contractions and longitudinal muscular contractions so as to promote a localized increase in the flow of blood is not disclosed.

Without wishing to be limited by theory, the inventor attributes the enhanced flow of blood to a timed succession of electrically-induced muscular contractions, the succession including at least one radial contraction followed by at least one longitudinal contraction. Preferably, the electrical signals that precipitate the longitudinal contraction should be timed such that the radial contraction is still at least partially in effect, as shown by the dashed or solid lines 40a, 42a, and 44a in FIGS. 2C-2E. It is known that muscle tissue fundamentally differs from an ideal resistor in that a muscle is an extremely complex resistor having an inherent lag time, after providing the requisite electrical stimulation, until contraction occurs, and having an inherent lag time, after stopping the stimulation, until contraction completely subsides. The present invention utilizes the inherent relaxation lag time after stopping (or reducing) the stimulation to the limb segment. The radial contractions greatly reduce the fluid communication between the downstream vessels below the constriction point and the upstream vessels disposed above the constriction point (i.e., closer to the heart on the blood flowpath). This phenomenon contributes to the efficacy of the longitudinal contraction, in which much of the blood in the arteries in the limb segment is forced out of the limb segment. Since the return flowpath to the heart is temporarily closed or constricted, the blood in the limb segment is forcefully driven into the blood/oxygen-deficient extremities, which has become the path of least resistance.

Alternatively or additionally, switching mechanism 18 can also be configured as a distributing mechanism that simultaneously distributes a positive voltage to two or more electrodes, or a negative voltage to two or more electrodes, as shown in FIG. 2E, where radial contraction 44a is induced, at least partly, by the voltage differential that is delivered to electrodes 20c and 20d concurrently with the voltage differential that is delivered to electrodes 20d and 20a.

Referring again to FIGS. 2B-2E, a localized decrease in the flow of blood can be achieved by substantially reversing the sequence described hereinabove. Thus, by way of example, radial contraction 44 of FIG. 2D is induced, followed by longitudinal muscular contraction 42 of FIG. 2C.

FIG. 3 is a diagram showing an exemplary switching arrangement for switching mechanism 18, and the electrical connections between switching mechanism 18, signal generator 10, and surface electrodes 20a-d. Signal generator 10 and switching mechanism 18 are electrically connected by a positive electrical connection and by a negative electrical connection. The negative electrical connection connects to a first switch 24a having terminals $T_1$-$T_4$, by means of rotating electrical connector 26*a*, and the positive electrical connection connects to a second switch 24*b* having terminals $T_5$-$T_8$, by means of rotating electrical connector 26*b*. As described hereinabove, switching mechanism 18 can have an additional electrical connector (e.g., electrical connector 28*b*) for concurrently providing two or more positive electrical connections, or two or more negative electrical connections, so as to distribute a positive voltage between two or more electrodes, or to distribute a negative voltage between two or more electrodes.

In the switch positions depicted in FIG. 3, signal generator 10 is negatively connected, via terminal $T_1$, to electrode 20*a*, and positively connected, via terminal $T_6$, to electrode 20*b* (assuming that optional connector 28*b* is not connected). In these switch positions, electrodes 20*c* and 20*d* are not electrically connected. Thus, with signal generator 10 connected to a power supply, and with stimulation device 50 disposed on a limb segment such as lower leg 200, as shown in FIG. 2A, a voltage differential between electrodes 20*a* and 20*b* would effect a radial contraction of the muscles.

Figure 4:
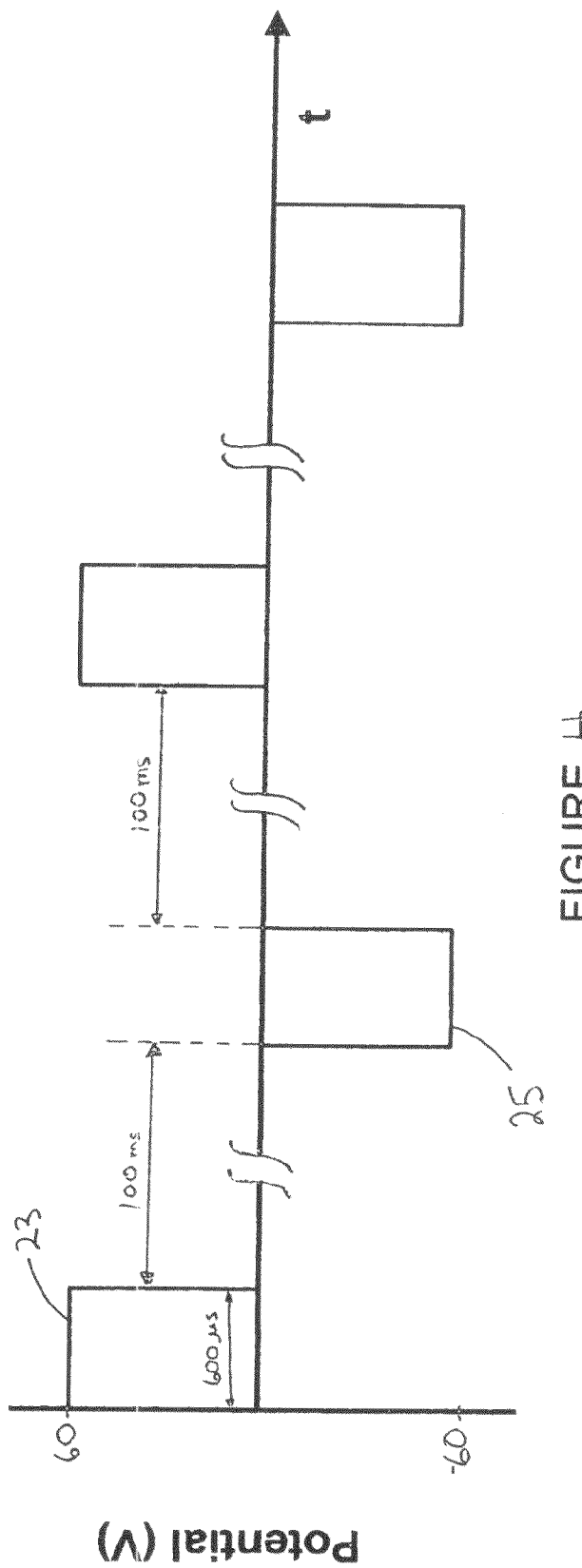
FIG. 4 is an exemplary voltage vs. time graph, according to the inventive treatment method and device of the present invention.

FIG. 4 shows an exemplary voltage vs. time graph for a treatment method according to the present invention, using the inventive device described hereinabove. The impulses provided are square waves having an intensity of 60 Volts. The duration of each square wave is approximately 600 microseconds. The time axis has not been drawn to scale, in order to fit 2 full cycles in the graph.

Typically, each step described with respect to FIGS. 2B-2E includes 3-30 of such impulses.

The time interval between positive impulses (or between negative impulses) is approximately 100 milliseconds. Thus, the cycle frequency (one positive and one negative impulse) is about 10 cycles per second, i.e., about 10 Hz. Although only 4 impulses are shown in FIG. 4, it will be appreciated that a practical treatment requires a large plurality of such impulses.

The initial impulse 23 provided to electrode pair 20*a* and 20*b* by signal generator 10 has a positive voltage differential (+60 Volts). The second impulse 25 applied to electrode pair 20*b* and 20*c* by signal generator 10 has a negative voltage differential of −60 Volts.

More generally, the voltage differential is up to 80V, and more typically, 30-60V, depending, inter alia, on the impedance of the patient's skin. The cycle frequency is 0.5-20 Hz, more preferably, 6-15 Hz.

Preferably, signal generator 10 is designed and configured to deliver the electrical signals at a rate of 1-30 periods per minute, and more preferably, 5-20 periods per minute.

As used herein in the specification and in the claims section that follows, the term "period", with regard to electrical signals delivered to the electrodes, refers to a repeating sequence, between at least three electrodes, of at least one radial contraction and at least one longitudinal contraction, effected at least partially in series. Thus, Step I, Step II, Step III, and Step IV, as described hereinabove, followed by Step I, Step II, Step III, and Step IV, represents two periods. A sequence of Step I, Step II, Step I, Step II, Step I, Step II, represents three periods. The term "repeating sequence" is meant to include semi-repetitive sequences. Thus, the sequence of Step I, Step II, Step III, and Step IV, followed by Step I, Step II (without Step III and Step IV), followed by Step I, Step II, Step III, and Step IV, represents three periods.

As used herein in the specification and in the claims section that follows, the term "upstream", with regard to a first position in the blood flowpath of a body, refers to a position that is closer to the heart, along the blood flowpath. Similarly, the term "downstream", with regard to a first position in the blood flowpath of a body, refers to a position that is farther from the heart, along the blood flowpath.

As used herein in the specification and in the claims section that follows, the term "another electrode", with respect to a plurality of at least a first, second and third electrode for operatively contacting a limb segment of a body, refers either to the first electrode, or an additional electrode (such as a fourth electrode) other than the second and third electrodes.

As used herein in the specification and in the claims section that follows, the term "time-distinct impulse" and the like, is meant to refer to the non-overlapping incidence of consecutive (or adjacent) electrical impulses, as shown, by way of example, in FIG. 4 hereinabove.

As used herein in the specification and in the claims section that follows, the term "voltage differential" refers to an absolute difference between two distinct voltage values.

As used herein in the specification and in the claims section that follows, the term "radial muscle contraction" and the like, with respect to a limb segment, refers to an instrumentally induced muscle contraction that is perpendicular or generally perpendicular to the general flowpath of blood through the limb segment, or results from a voltage differential radially applied between electrodes on the limb segment.

As used herein in the specification and in the claims section that follows, the term "longitudinal muscle contraction" and the like, with respect to a limb segment, refers to an instrumentally induced muscle contraction that is parallel or substantially parallel to the general flowpath of blood through the limb segment, or results from a voltage differential longitudinally applied between electrodes on the limb segment.

It must be emphasized that various frequencies and wave forms have been found to be effective in conjunction with the method of the present invention. Appropriate wave forms include square waves, waves of transcendental functions, spikes, linear functions, and stepped patterns. Frequencies vary greatly, depending on the general health of the client, the type and duration of the treatment, etc. Hence, it is preferable that the device be configured such that an experienced operator can adjust, with facility, various parameters, including wave form, frequency, and intensity, by means of microprocessor 14.

The frequency, the number, the intensity and the duration of muscle contractions are controlled by the nature of the signals passed to the electrodes. The localized increase in the flow of blood effected by the device and method of the present invention is important for a wide variety of medical applications, including but not limited to rehabilitating muscular response affected by trauma or inactivity, decreasing the amount of water retained, as in case of the lower limbs, improving blood and lymph circulation, thereby alleviating pain, therapy related to controlling the function of erectile tissue, and speeding up healing, particularly in the case of diabetic patients. The restriction of blood flow by inducing the repeated contractual movement of muscular tissue against the natural flow of blood is also germane to a wide variety of medical applications, including various surgical procedures and edema reduction.

Figure 4A:
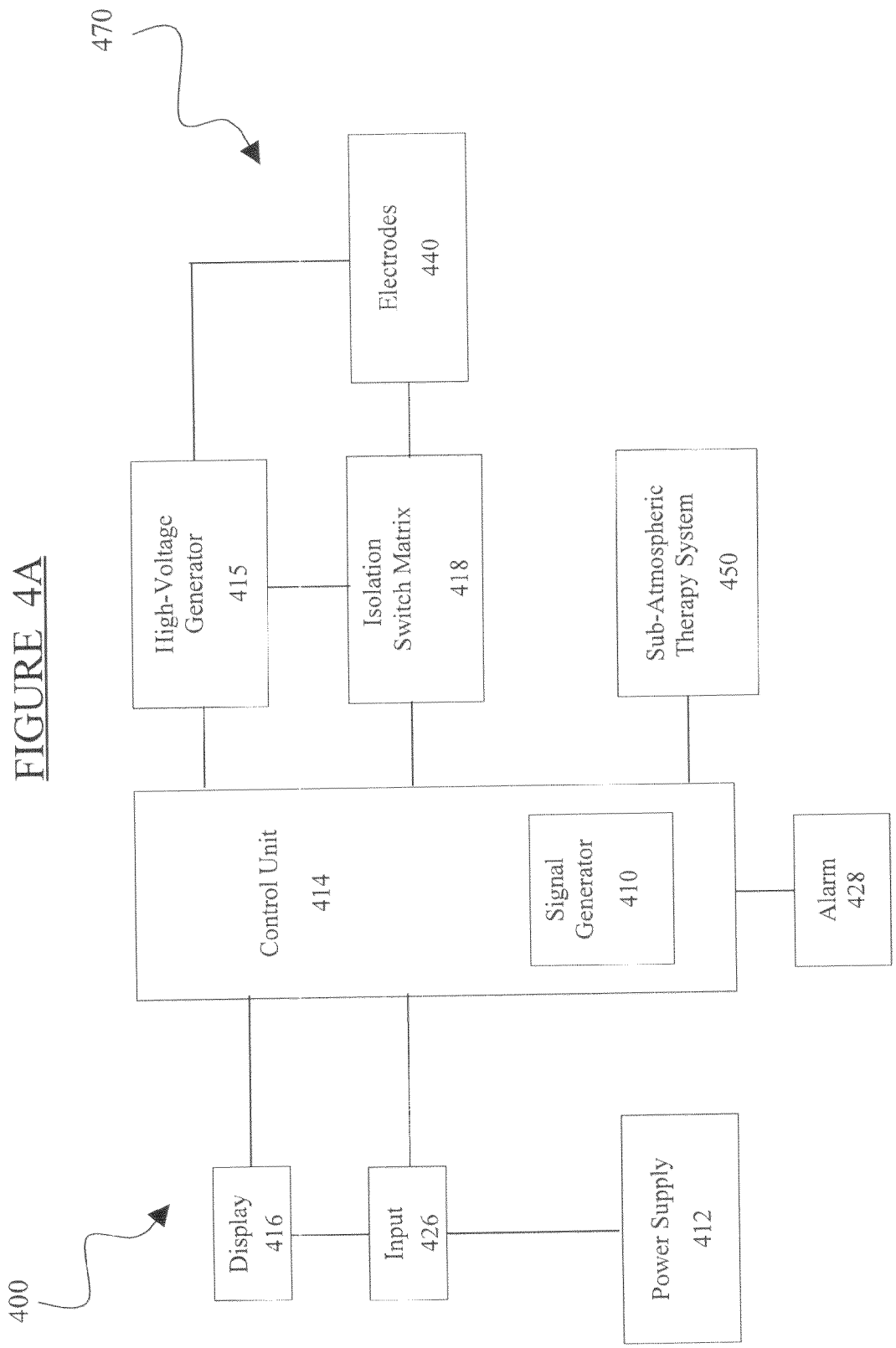
FIG. 4A provides a schematic representation of one aspect of an integrated device or apparatus of the present invention, including both a sub-atmospheric therapy apparatus and a muscle pump device.
Figure 4B:
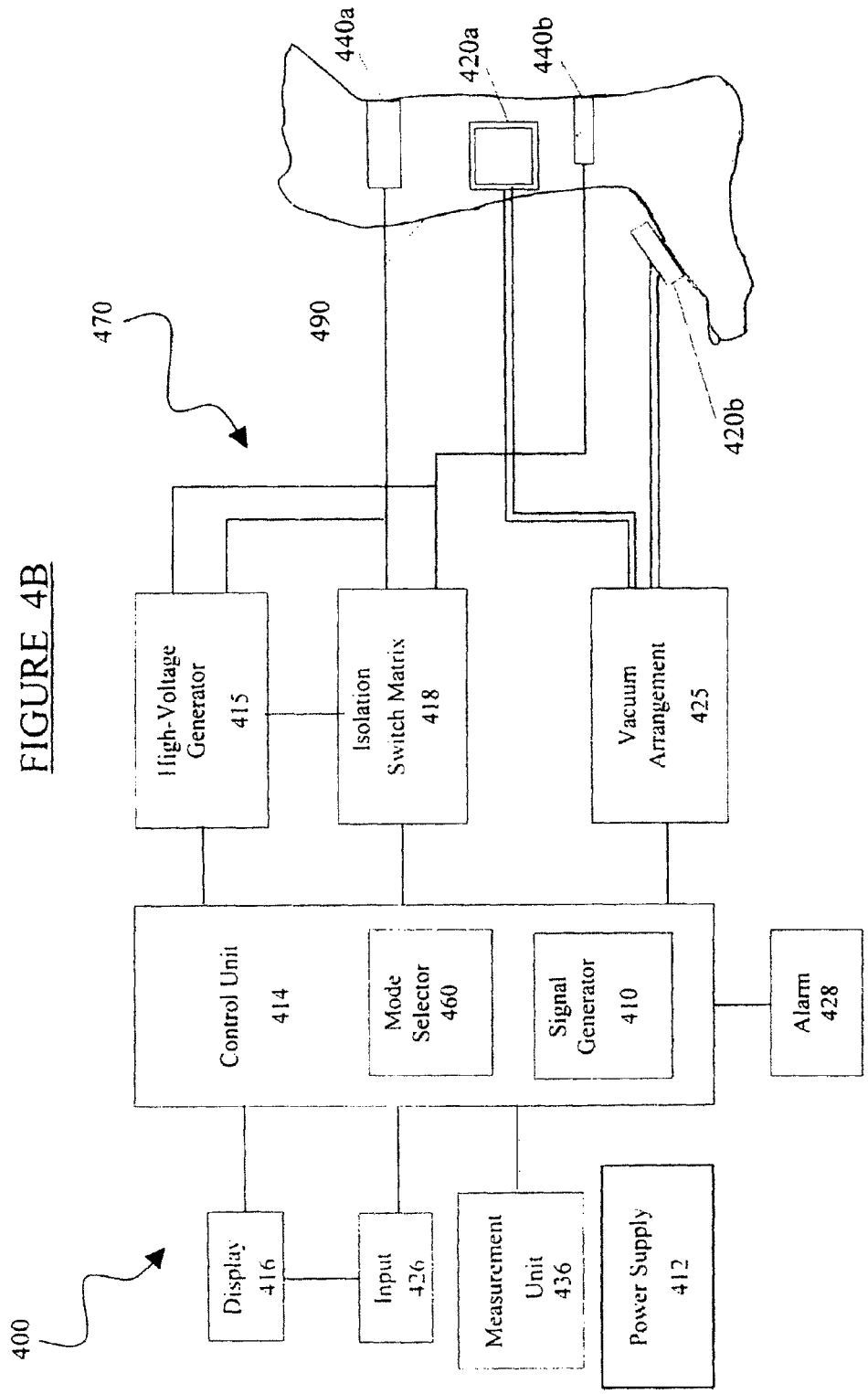
FIG. 4B provides a schematic representation of the integrated device of FIG. 4A, disposed on a limb of a subject.

Another embodiment of the device and method of the present invention may be better understood with reference to FIGS. 4A and 4B. FIG. 4A provides a schematic representation of one aspect of an integrated device or apparatus 400, including a muscle pump or stimulation device 470 that may be similar or substantially identical to the stimulation device described hereinabove, along with a sub-atmospheric therapy system or apparatus 450. FIG. 4B provides a schematic representation of device 400, disposed on a limb of a subject, by way of example, a lower leg. A power supply 412 may provide power to a high-voltage generator 415, a control unit 414, a signal generator 410, a display 416, an input or inputting device 426, an alarm or alarm device 428, a switching mechanism such as an isolation switch matrix 418, and to sub-atmospheric therapy apparatus 450. Control unit 414 may be connected to, or may communicate with, both sub-atmospheric therapy apparatus 450 and various components of stimulation device 470, such as high-voltage generator 415, signal generator 410, display 416, input 426, alarm 428, and switch matrix 418. Electrodes 440 may be connected to control unit 414 via switch matrix 418, or via high-voltage generator 415.

Although signal generator 410, as shown, is disposed within control unit 414, it will be appreciated that signal generator 410 may be disposed outside control unit 414. It will be further appreciated that display 416 and input 426 may serve both sub-atmospheric therapy apparatus 450 and muscle pump or stimulation device 470.

Control unit 414 may be connected to the various controlled components using analog, discrete, and/or serial I/O signals, according to the requirements of the interfaces of the respective components. It will be appreciated that the communication mechanism may include an electronic network of various designs, including serial bus or parallel bus architectures.

Control unit 414 may effect automated control of sub-atmospheric therapy apparatus 450 and stimulation device 470 for a variety of treatment protocols.

With specific reference now to FIG. 4B, a lower leg 490 of a subject has a surface wound, such as a surface wound disposed on the calf, and/or a surface wound disposed on the instep. Each of these surface wounds may be covered by a wound covering and sealing arrangement that includes wound cover and sealing arrangements 420a and 420b, respectively. As described, vacuum arrangement 425 provides suction to the volume defined by a wound cover and sealing arrangement (such as arrangement 420a) and the surface of the limb thereunder, responsive to control unit 414, so as to achieve a sub-atmospheric pressure within that volume.

The efficacy of the sub-atmospheric pressure therapy may be limited by the rate at which arterial blood—containing oxygen, nutrients, white blood cells, and other constituents—is delivered to the area around the wound. For patients having a compromised arterial circulatory status as evidenced by low ABI index and or low ankle blood pressures, such therapy may be of extremely limited value. Additionally, poor venous return and compromised lymphatic drainage contribute to poor healing by preventing "waste products" from being evacuated from the area.

We have found, however, that various mechanical compression methods for locally resolving these concerns to be unsuitable, and possibly deleterious, for use in conjunction with sub-atmospheric pressure therapy, particularly in the case of patients having evidence of arterial, venous and/or lymphatic circulatory compromise. These compression techniques may result in multiple untoward effects including pain, compromise of the circulation, and general reduction in the ability of the patient to engage in normal activities during treatment. By sharp contrast, we have found that by stimulating the local muscle tissue using electrical impulses via the neural motor points, a significant increase in the afferent and efferent flow of blood in the vicinity of the wound may be safely achieved. Without wishing to be bound by theory, we believe that electrically stimulated muscle movement gently and rhythmically alters the configuration of the local blood vessels to increase the local flow of blood. The muscle movement is effected from within the limb, such that skin and surface wound issues are mitigated. In stark contrast, in the various external compression techniques, the driving force—compression—is delivered from outside the surface of the body, such that the skin and wound area lie between the driving force and blood vessels such as deep veins within the limb, and must therefore disadvantageously absorb and transfer the compressive forces.

In one preferred embodiment, the electrical stimulation of the local muscle tissue is performed to effect improved venous return and lymphatic drainage.

In another preferred embodiment, the electrical stimulation of the local muscle tissue is performed to promote at least the local arterial flow.

Stimulation device 470 includes at least two electrodes 440a, 440b adapted to be disposed on the skin surface of the patient. Electrodes 440a, 440b may be fabricated from a conventional conducting foil and a conducting hydrogel adhesive, or from various other conducting medium that will be readily apparent to one of ordinary skill in the art. Various electrodes used in transcutaneous electrical nerve stimulation (TENS) pain reduction devices may be particularly suitable.

While switch matrix 418 may enable the use of at least three, and typically, at least four electrodes, the present invention is capable of operating without such a switch matrix, and with a minimum of two electrodes.

Electrodes 440a, 440b are placed on the skin surface of the subject. The general size, shape, and placement of electrodes 440a, 440b are advantageously determined to achieve superior stimulation of the particular underlying muscles. In the case of lower leg 490 shown in FIG. 4B, the most important underlying muscles include the soleus and gastrocnemius muscles.

Typically, electrodes 440a, 440b may be disposed on either side (e.g. on an upstream side and a downstream side, with respect to the venous return/lymphatic drainage) of the wound, such as on either side of a surface wound covered by cover arrangement 420a. However, an appreciable increase in the flow of blood to the wound area may be achieved even when the wound area is not between the electrodes, and is upstream, with respect to the venous return, from the electrodes. By way of example, electrodes 440a, 440b are both disposed downstream of the wound on the instep, covered by cover arrangement 420b. Upon activating muscle pump 470, venous return and lymphatic drainage may be enhanced, and fluid pressure, and associated pain within the foot may be at least partially alleviated. Furthermore, the stimulated muscles are in the calf, far removed from the instep, such that vigorous contraction of the muscles may be effected without causing discomfort to the instep area.

Thus, according to one aspect of the present invention there is provided an apparatus for facilitating the healing of a wound on a limb of a body of a subject, the apparatus including: (a) a wound treatment assembly having: (i) a wound cover adapted to cover an area above the wound; (ii) a sealing arrangement, associated with the cover, adapted to contact and at least partially seal a volume beneath the cover from an ambient environment; (iii) a vacuum mechanism fluidly communicating with the volume, and adapted to produce a sub-atmospheric pressure within the volume; (b) a muscle contraction device having at least a first electrode and a second electrode, adapted to operatively contact the limb; (c) a control unit, adapted to connect to a power supply and operatively connected to each the electrode, the control unit further adapted to provide, via the electrodes, a sequence of electrical impulses to neural motor points associated with the limb, whereby muscle tissue associated with the neural motor points contracts to effect a localized increase in a flow of blood through a blood vessel in the limb, the control unit being operatively connected to the wound treatment assembly and further adapted to control an operation of the treatment assembly.

The control unit may have a first operating mode enabling a combined treatment protocol including both operation of the wound treatment assembly and operation of the muscle contraction device. The combined treatment protocol may include simultaneous operation of the wound treatment assembly and the muscle contraction device, or including at least intermittent operation of both the wound treatment assembly and the muscle contraction device.

We have found that many patients, particularly those having a low ABI index, are largely insusceptible to muscle fatigue due to lengthy muscle contraction treatments. This may, in turn, enable lengthy sub-atmospheric treatments of at least 2 to 3 hours, in some cases, at least 6 hours, or even substantially continuously. We have further found that in some cases, the length of the treatment may be extended by intermittently operating the muscle contraction device at a lower than optimal intensity. By doing so, increased blood flow may be sustained over continuous operation (at least 6-24 hours, possibly more), while benefitting from concurrent operation of the sub-atmospheric pressure therapy.

The control unit may advantageously be disposed in a single housing.

The control unit may be configured to implement the combined treatment protocol responsive to a pre-determined sequencing. The control unit may be configured to receive the pre-determined sequencing via an input unit such as input unit 426.

The control unit may have an additional operating mode enabling a treatment protocol including solely operation of the wound treatment assembly, and/or an additional operating mode enabling a treatment protocol including solely operation of the muscle contraction device. The control unit may also have a mode selection switch such as mode selection switch 460, for selecting between the various operating modes.

The control unit may be configured to prompt a user for an ankle-brachial index (ABI) or lower extremity blood pressure of the subject. For example, responsive to an ABI and/or blood pressure below pre-determined values, the control unit may be configured to perform at least one safety operation, including but not limited to producing a warning signal, displaying a recommended treatment protocol, and/or disabling an option of operating the wound treatment assembly without the muscle contraction device. In various circumstances, the control unit may activate alarm 428.

The control unit may be configured to control various parameters pertaining to the vacuum arrangement, including a depth of vacuum produced by the vacuum mechanism. Various other control functions pertaining to the vacuum arrangement will be recognized by one of ordinary skill in the art.

The inventive apparatus may further include a measurement unit 436 adapted to produce at least one measurement of a parameter associated with blood flow in the subject. The control unit may be configured to perform at least one safety operation or other operation responsive to this measurement. Examples of such measurement units include:

blood velocity measurement, e.g., using a Doppler instrument;

on-line ABI measurement (can be input or directly transferred to the control unit), preferably including the identified ankle blood pressure of the affected lower extremity;

RTS (Refill Time Sensor)—measures cyclic changes in the leg (limb) volume due to blood flow (inflow and reflux) using body impedance plethysmography measurements;

MCS (Muscle Contraction Sensor)—measures the magnitude of muscle contraction to provide, inter alia, direct feedback on the physical placement of the electrodes, and effective treatment with reduced user discomfort through the modification of the electrical signal characteristic (e.g. current intensity, pulse train modulation etc.);

LTS (Limb Temperature Sensor)—measures the limb border temperature to provide a clinical treatment indication (e. g., for PAD);

UAS (Ultrasound Artery Sensor)—measures arterial blood flow, e.g., by means of a miniature ultrasonic transducer, to provide quick, direct feedback regarding therapy efficacy.

Using the apparatus and method of the present invention, patients having a characteristically low ABI, below 0.8, below 0.7, below 0.6, below 0.5, and in some cases, as low as about 0.3, may be efficaciously treated with the sub-atmospheric pressure therapy, and substantially without risk, or with significantly reduced risk of infection. In some cases, however, the ABI is not an accurate measurement, and a toe brachial index (TBI) may be used. TBI is a calculation based on the systolic blood pressures of the arm and the systolic blood pressures of the toes. The examination is similar to the ABI except that it is performed with a photoplethysmograph (PPG) infrared light sensor and a small blood pressure cuff placed around the toe. A TBI of 0.8 or greater is considered normal.

We have further discovered that a localized increase in a venous flow of blood in an extremity or in a peripheral region of the body can be achieved by compounding electrical stimulation of the natural venous muscle pump with external pressure, more specifically, a compression unit such as a compression garment or compression bandage. While compression garments may provide a modest benefit in augmenting superficial venous flow, such compression garments are generally known to be ineffective in improving the flow of blood through the underlying deep veins.

At least a portion of at least one electrode of the electrical stimulation device may be disposed underneath the compression unit, between the compression unit and the calf of the leg being stimulated. The electrode may be completely disposed underneath the compression unit.

Preferably, the compression garment or bandage may be adapted and disposed, with respect to the electrodes, such that pressure is delivered to the calf in substantially the same location as the contraction of the superficial muscle takes place. If, by way of example, the electrical stimulation contracts the gastrocnemius muscle, the compression garment delivers pressure to the calf to that gastrocnemius muscle. Preferably, the compression unit delivers pressure to the calf at the central point or region of the gastrocnemius muscle contraction.

We have further discovered that the use of external pressure on a conical limb segment, to augment the effect of the electrical stimulation of the natural venous muscle pump, may, under particular conditions, achieve substantially no additional localized increase in a venous flow of blood, with respect to the electrical stimulation alone. More surprisingly, the use of external pressure to compound the electrical stimulation of the natural venous muscle pump may, in some circumstances, actually impair the performance of the electrical stimulation device, such that the venous flow of blood, with respect to the electrical stimulation alone, is actually reduced. This phenomenon may occur when the maximal pressure exerted by the compression unit is above 60 mmHg, above 50 mmHg, or above 40 mmHg. In some cases, for example, in patients having weak muscles, this phenomenon may occur when the maximal pressure exerted by the compression unit is above 35 mmHg. Below these maximal pressure levels, however, the use of external pressure to compound the electrical stimulation of the natural venous muscle pump may be particularly efficacious.

Without wishing to be bound by theory, we believe that at relatively high compressive pressures, the pressure delivered to the walls of the veins is sufficiently high to constrict the flow therethrough, such that the pressure is a deleterious influence on the action of the electrical stimulation on the venous muscle pump. This problem may be significantly more pronounced in patients having a weak natural venous muscle pump.

Figure 5:
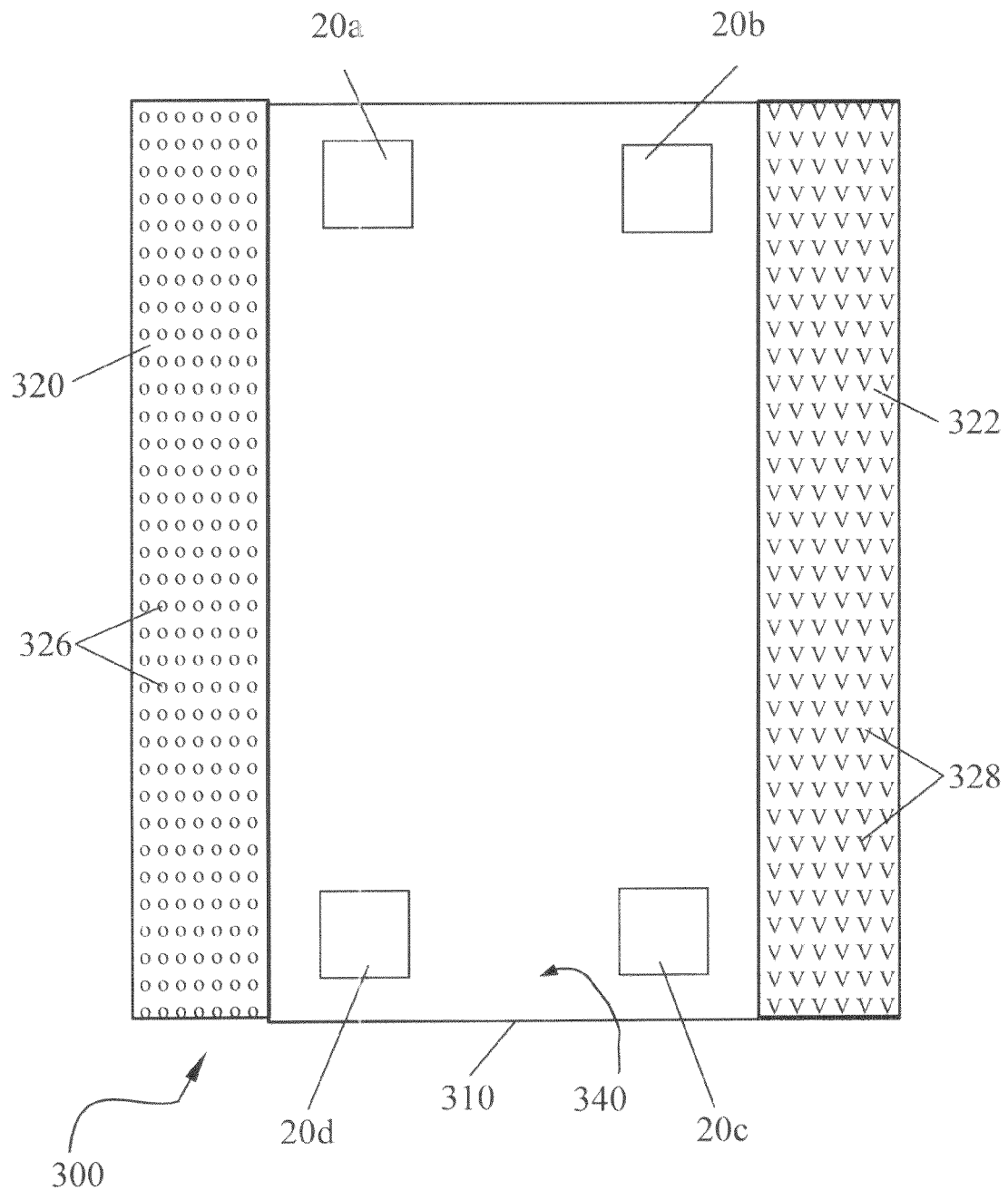
FIG. 5 is a schematic side view of an exemplary compression device that may form a portion of the device of the present invention.

FIG. 5 is a schematic side view of an exemplary compression device 300 that may form a portion of the device of the present invention. Compression device 300 includes a flexible sheet 310 that may be generally rectangular. On a first, inside face 340 of flexible sheet 310 are disposed electrodes, such as electrodes 20a-d, which may be secured to flexible sheet 310 by various fastening elements and arrangements known in the art.

The flexible sheet is designed and dimensioned to at least partially envelope a limb segment of the user. By way of example, flexible sheet 310 is designed and dimensioned to substantially completely envelope a limb segment such as the lower leg of the user.

Compression device 300 may be wrapped around the limb segment and tightly secured to the limb segment using fastening elements and arrangements known in the art, including various complementary fastening arrangements, depending on the desired pressure and other considerations. In FIG. 9, flexible sheet 310 is equipped with an exemplary loop and hook fastening arrangement having a first region 320 containing loops 326 and a second region 322 containing hooks 328. Typically, second region 322 is disposed on the first face of flexible sheet 310, and first region 320 is disposed on the opposite face (denoted by dashed lines) of flexible sheet 310, such that first and second regions 320, 322 overlap and contact each other, thereby fastening loops 326 and hooks 328.

Additional pressure on the limb segment may be developed by donning a compressive garment or sock on top of compression device 300. FIG. 4 shows a schematic cross-sectional view of such a compressive sock 400, disposed on a leg 450 of the user.

Figure 5A:
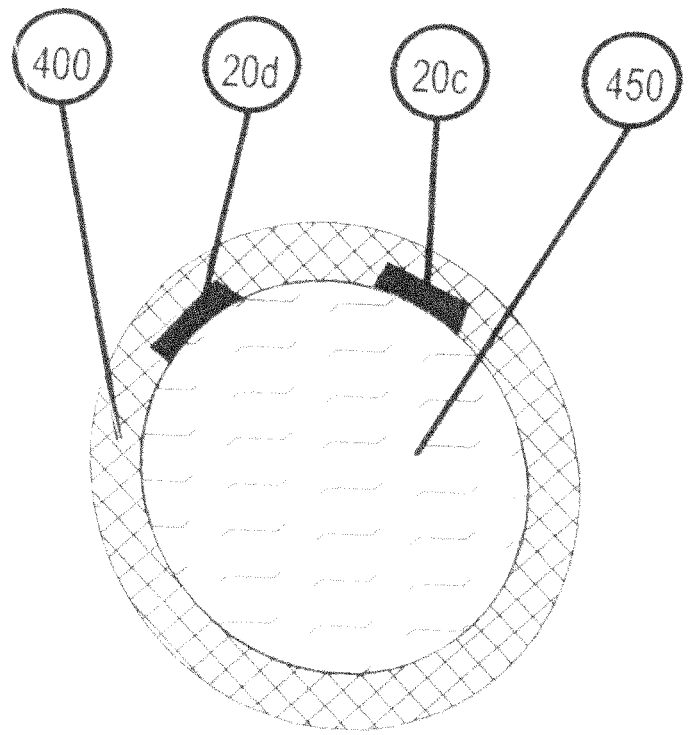
FIG. 5A provides a schematic, cross-sectional view of a compressive sock that may be donned directly on the limb segment, in accordance with the present invention.

Alternatively, and as shown in FIG. 5A, compressive sock 400 may be donned directly on the limb segment, with no additional compression device disposed therebetween. Compressive sock 400 may cover, or at least partially cover, the electrodes such as electrodes 20c and 20d.

Various types of constant support and constant compression bandages are known in the art, and may be used as part of the device and method of the present invention. Light support bandages, including various crepe-type arrangements, have seen use in preventing edema formation.

More typically, light compression bandages may be used for this purpose. Light compression bandages may provide and maintain low levels of pressure, up to 20 mmHg on an ankle of average dimensions.

Moderate compression bandages may be used to apply compression of about 30 mmHg. High compression bandages may be used to apply high levels of compression of about 40 to 50 mmHg on an ankle of average dimensions. Some compression bandages are capable of applying pressures in excess of 55 or 60 mmHg.

Figure 5B:
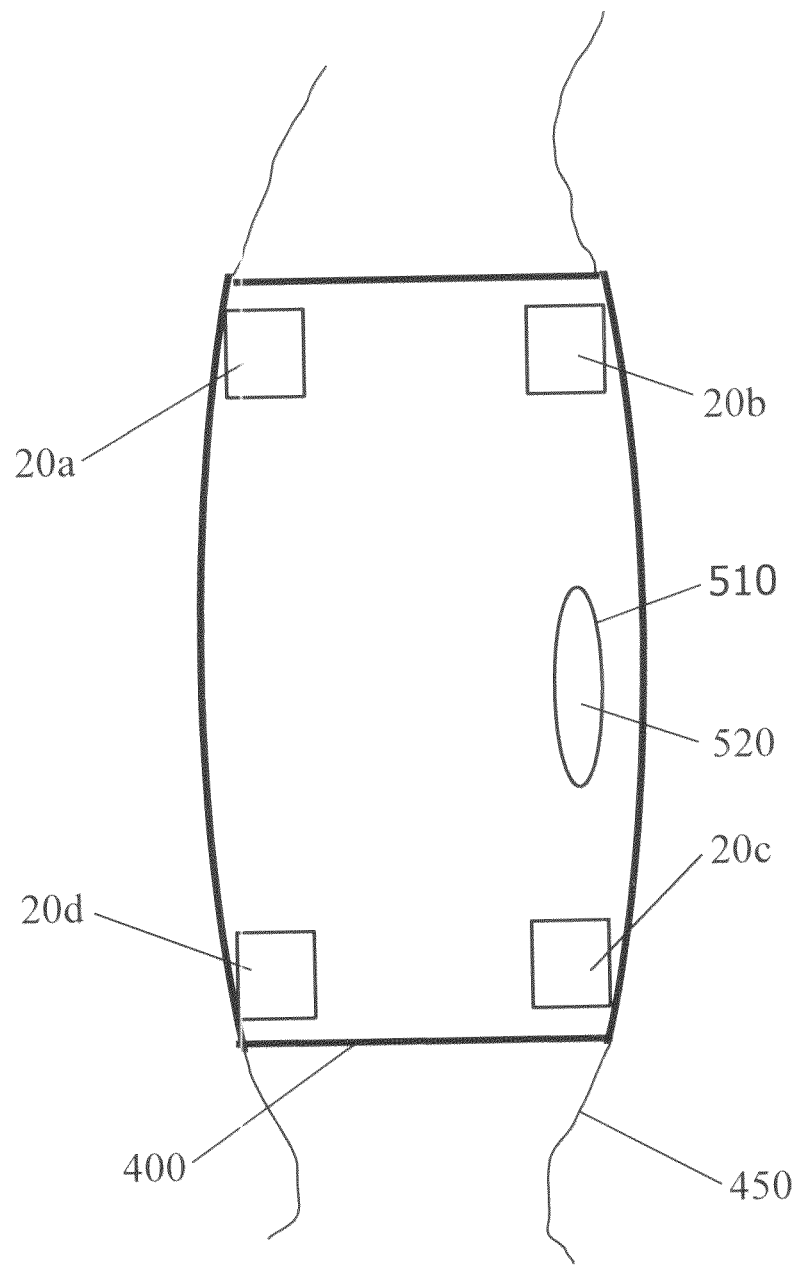
FIG. 5B shows a schematic side view of the inventive compressive sock of FIG. 5A, disposed on a leg of the user.

FIG. 5B shows a schematic side view of compressive sock 400, disposed on leg 450 of the user. Electrodes 20a-20d are disposed on leg 450, underneath compressive garment, sock or bandage 400. When the electrical stimulation unit is activated to contract at least one muscle on leg 450, a region of contraction 510 having a geometric center of contraction 520 is formed.

Preferably, compressive sock 400 covers, and delivers a compressive pressure to, the surface of at least a portion of region of contraction 510. As shown in FIG. 9B, compressive sock 400 covers, and delivers a compressive pressure to, the surface of center of contraction 520.

The inventive device using electrical stimulation compounded by external pressure may be used on various limb segments on the body, including, but not limited to, the forearm, upper arm, and the foot, including the sole of the foot. Compression device 300 and compressive sock 400 may be specifically designed and configured to effectively envelope, and deliver pressure to, the surface of particular conical limb segments.

The compression hosiery, bandages, and the like used in accordance with the present invention advantageously deliver a compressive pressure of at least 5 mmHg, and more typically, at least about 8 mmHg.

The frequency, number, intensity and duration of muscle contractions may be heavily influenced by the nature of the signals passed to the electrodes.

Figure 5C:
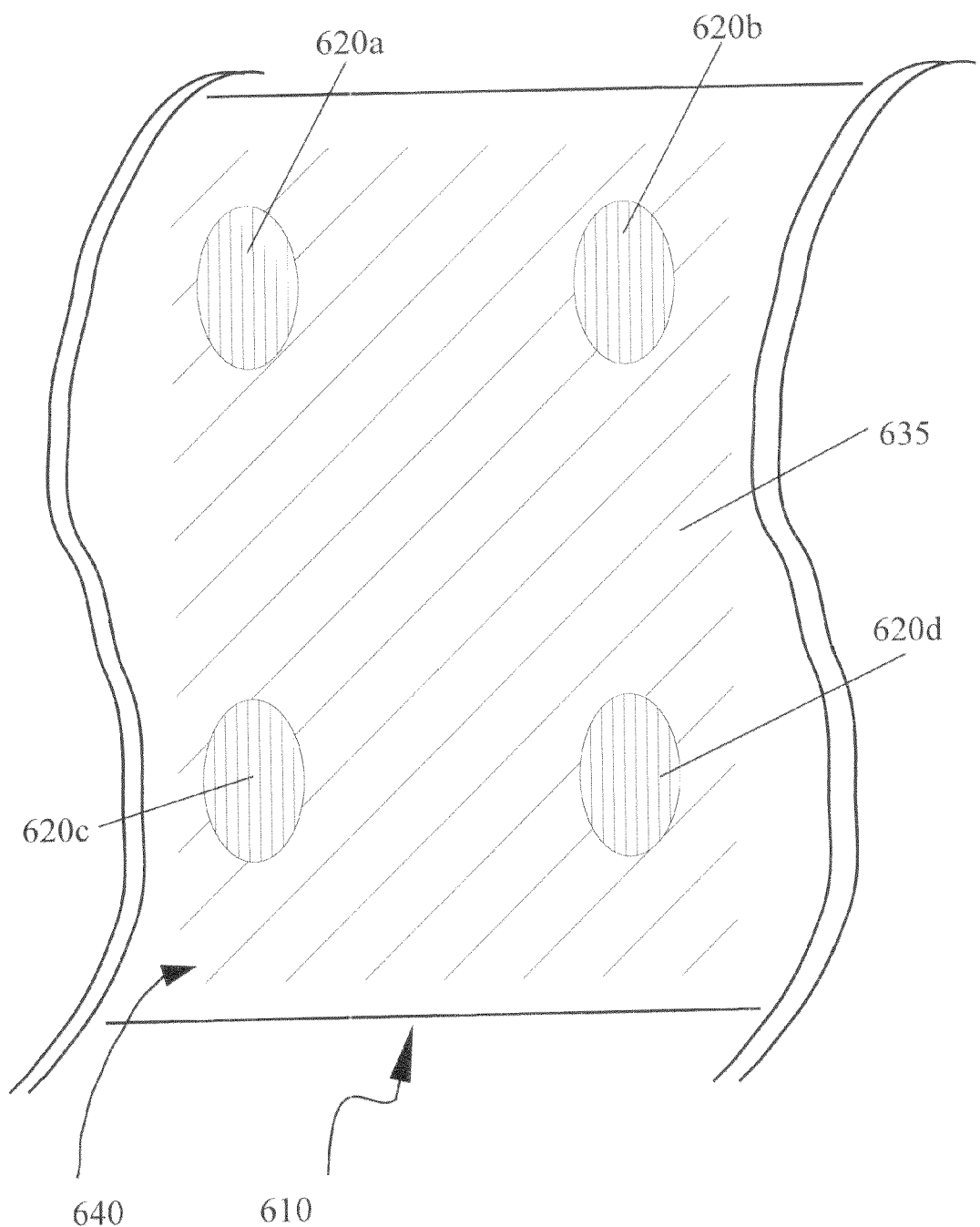
FIG. 5C is a schematic perspective view of a portion of an inside face of a device of the present invention, in which surface electrodes are embedded.

FIG. 5C shows a schematic perspective view of a portion of an inside or inner face 640 of a device of the present invention. Inside face 640 includes an inner face 635 of a flexible sheet 610 of at least one elastic compression garment or compression bandage. Attached to, and/or embedded in inside face 640 are surface electrodes 620a-620d.

Figure 5D:
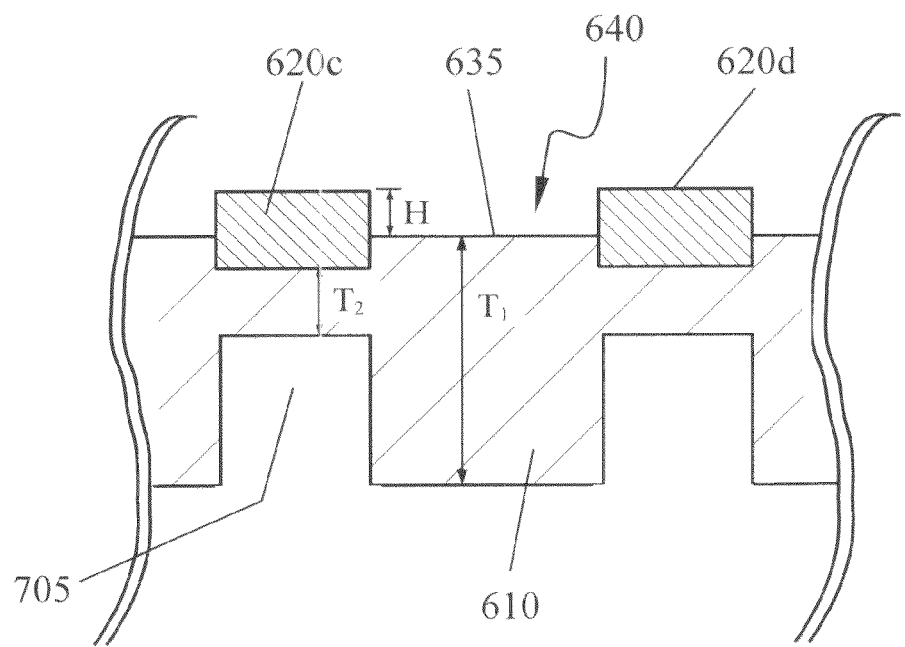
FIG. 5D is a schematic, cross-sectional view of a portion of the inside face of FIG. 5C, the compression garment or bandage having a recess or void volume behind the electrodes.

FIG. 5D is a schematic cross-sectional view of a portion of inside face 640 of FIG. 5C. Inside face 640 includes inner face 635 of a flexible sheet 610 of the elastic compression garment or bandage. Attached to, and/or at least partially embedded within inside face 640 are the surface electrodes. In the particular cross-section of FIG. 5D, surface electrodes 620c and 620d are shown, partially embedded in flexible sheet 610.

We have found that the protrusion of surface electrodes 620a-620d (only electrodes 620c-620d may be viewed) away from the inside face may cause mild discomfort to a relatively healthy user, and even extreme discomfort to less healthy users, particularly those suffering from local ulcers, edemas, etc. Thus, it may be highly advantageous to recess the electrodes so that they are flush, or substantially flush with inner face 635 of flexible sheet 610. In the event that surface electrodes 620a-620d protrude from inner face 635 towards the surface of the limb segment, the protrusion height H may be preferably less than 0.6 mm, more preferably less than 0.4 mm, and most preferably less than 0.25 mm.

Alternatively or additionally, the thickness of flexible sheet 610 may be variable, whereby behind electrodes 620a-620d, the thickness $T_2$ of flexible sheet 610 is smaller than the thickness $T_1$ of flexible sheet 610 in an area surrounding electrodes 620a-620d (e.g., by having a recess or void volume 705 behind electrodes 620a-620d). Consequently, a second pressure exerted towards the limb segment via electrodes 620a-620d may be less than a first pressure exerted towards the limb segment in various areas of flexible sheet 610 surrounding electrodes 620a-620d. The first pressure may exceed the second pressure by at least 5 mm Hg, by at least 10 mmHg or by at least 15 mmHg.

Recess 705 may have a substantially larger surface area than the surface area of the electrode disposed therein. Consequently, the position of electrodes 620a-620d may be adjusted to suit the size and shape of leg segments of a wide variety of patients, such that the compression unit or garment may be of a universal nature.

The compression garment or bandage may be adapted whereby the superatmospheric pressure exerted by the electrodes may be less than 12 mmHg, less than 8 mmHg or less than 4 mmHg. This may be accomplished by means of recess or void volume 705. When multiple compressive bandage wraps are used, fewer wraps may be wrapped over electrodes 620a-620d to achieve this design criterion.

Typically, the thickness of the compression garment or bandage(s) above the electrodes may be less than the maximal thickness above the compression garment or bandage(s) by at least 2 mm, at least 1 mm, or at least 0.5 mm.

Figure 5E:
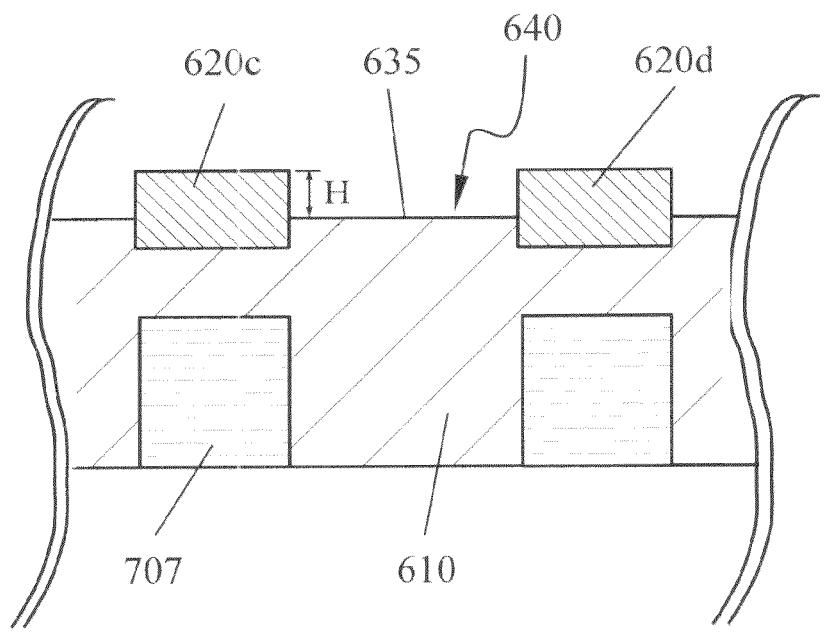
FIG. 5E is a schematic, cross-sectional view of a portion of the inside face of FIG. 5C, in which the recess of FIG. 5D is at least partially filled with a filler material, according to another embodiment of the present invention.

In another embodiment, provided in FIG. 5E in a schematic cross-sectional view, recess or void volume 705 of FIG. 5D is at least partially filled with a filler material 707, whereby, substantially as in the embodiment of FIG. 9D, the compressive forces or superatmospheric pressure acting on or through electrodes 620a-620d are reduced (typically by at least 5 mm Hg, by at least 10 mmHg or by at least 15 mmHg) with respect to the compressive forces or superatmospheric pressure delivered in various areas of flexible sheet 610 surrounding electrodes 620a-620d. Consequently, efficient, advantageous pressure may be exerted on the affected limb segment, without disadvantageously pressuring the tissue underneath the electrodes.

The localized increase in the flow of blood effected by the device and method of the present invention may be important for a wide variety of medical applications, including but not limited to alleviating CVI, inhibiting DVT, treating phlebitis, decreasing the amount of water retained, as in case of the lower limbs, improving blood and lymph circulation, thereby alleviating pain, and speeding up healing, particularly in the case of venous ulcers and the like. The restriction of blood flow by inducing the repeated contractual movement of muscular tissue against the natural flow of blood is also germane to a wide variety of medical applications, including various surgical procedures and edema reduction.

EXAMPLES

Reference is now made to the following examples, which together with the above descriptions, illustrate the invention in a non-limiting fashion.

Example 1

Figure 6A:
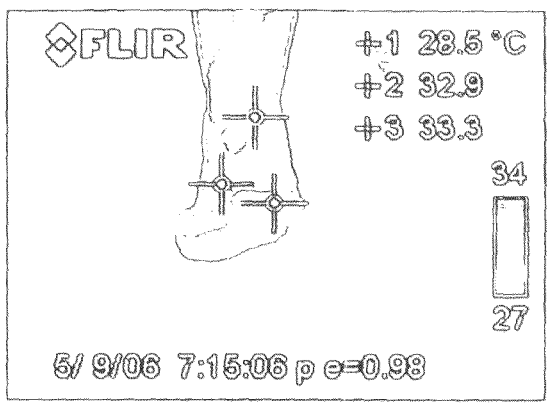
FIGS. 6A-6D are thermographs recorded intermittently during the course of a Transcutaneous Electrical Nerve Stimulation (TENS) treatment using a prior art TENS device.
Figure 6B:
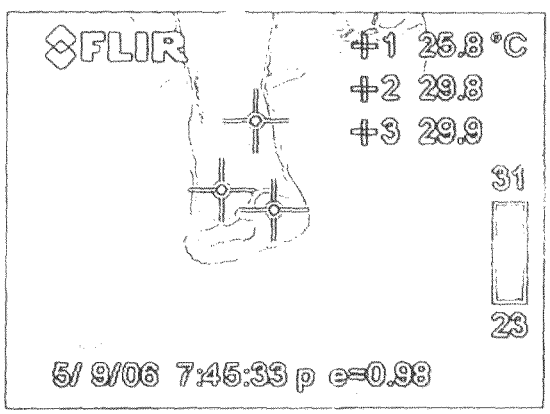
Figure 6C:
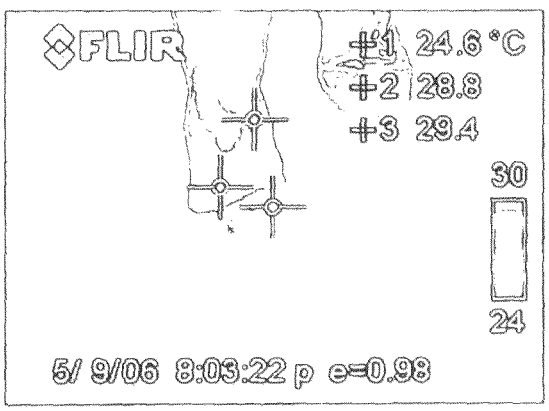
Figure 6D:
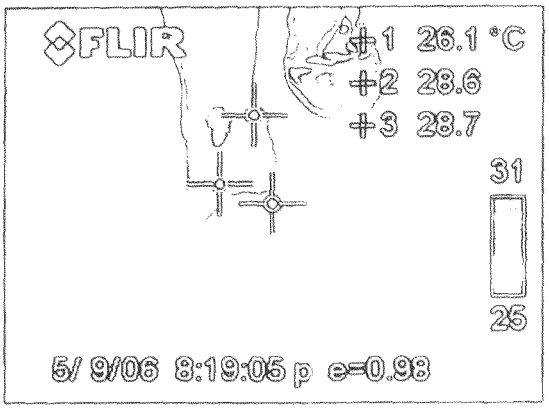
Figure 6E:
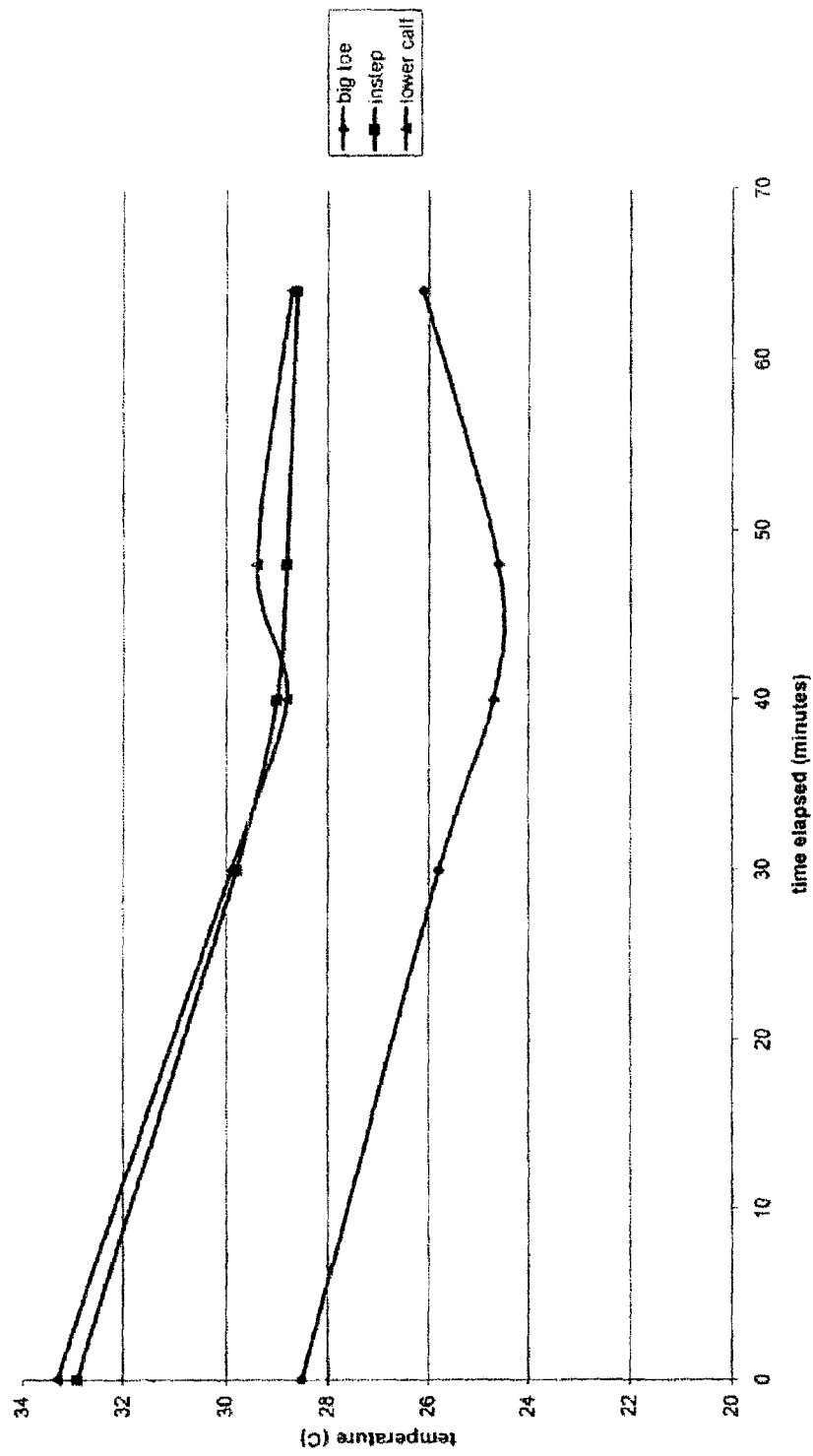
FIG. 6E is a plot of the temperature profile of three monitoring points on the foot, as a function of time, based, inter alia, on the thermographs of FIGS. 6A-6D.

A conventional Transcutaneous Electrical Nerve Stimulation (TENS) device was used to provide electrical stimulation to the lower leg of a patient suffering from poor circulation in the foot. A first surface electrode of the device was positioned underneath the knee, and a second electrode of the device was positioned above the calf. Electrical stimulation was administered for over 60 minutes. A FLIR™ ThermaCAM® EX320 was used to thermally monitor the foot and lower calf. In particular, three locations on the leg were monitored:
 (1) a point on the big toe;
 (2) a point on the instep;
 (3) a point on the lower calf.
Thermographs recorded intermittently during the course of the stimulation treatment are provided in FIGS. 6A-6D. Initially, the lower leg and calf regions, including lower calf point 3, are at a temperature of 33-34C; the instep, including instep point 2, is at a temperature of 33-34C; big toe point 1 is at 28.5C. After about 30 minutes, the temperatures in the toe, instep, and lower calf have not improved; if anything, a decrease of 2-3C is indicated. Subsequently, the temperatures at the three monitoring points remain fairly constant, such that after an hour, the temperature at big toe point 1 is still 2C below the initial temperature. The temperature profile of the three monitoring points is provided in FIG. 6E.

It is thus evident that this conventional (TENS) device and treatment method did not measurably increase the localized blood flow in the extremities of the stimulated leg.

Example 2

A device of the present invention was used to provide electrical stimulation to the lower leg of a patient suffering from poor circulation in the foot. Two surface electrodes of the inventive device were positioned underneath the knee, and an additional two surface electrodes of the device were positioned above the calf, substantially as shown in FIG. 2A. The microprocessor used for controlling the device was an ATMEL® 8 bit AVR® microcontroller, model no. ATmega8535, which also contains the signal generator unit.

Figure 7A:
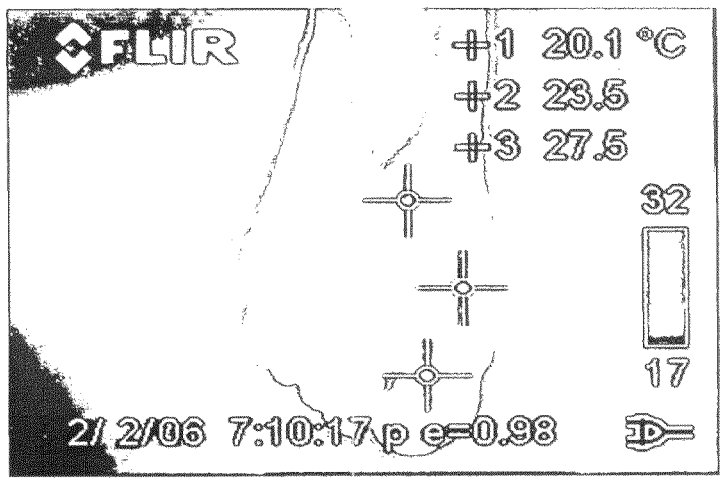
FIGS. 7A-7F are thermographs recorded intermittently during the course of an electrical stimulation treatment using the device of the present invention.
Figure 7B:
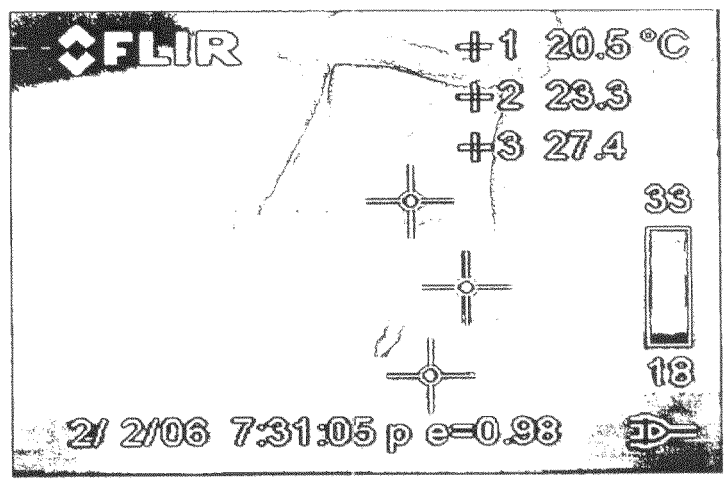

Electrical stimulation was administered for over 60 minutes. As in Example 1, a FLIR™ ThermaCAM® EX320 was used to thermally monitor the foot and lower calf. In particular, three locations on the leg were monitored:
 (1) a point on the big toe;
 (2) a point at the base of the big toe;
 (3) a point on the instep.
Thermographs recorded intermittently during the course of the stimulation treatment are provided in FIGS. 7A-7F. In the first thermograph provided in FIG. 7A, taken about 4 minutes after stimulation was initiated, the lower leg and calf regions (not shown) are at a temperature of at least 32C, instep point 3 is at a temperature of 27.5C; big toe base point 2 is at 23.5C, and big toe point 1 is at about 20C. In this thermograph image, all five toes are blue to deep blue, indicating a temperature of ~17-18C. The second thermograph (FIG. 7B), taken about 20 minutes later, is substantially identical to the first thermograph. A slight warming of the smaller toes is observed.

Figure 7C:
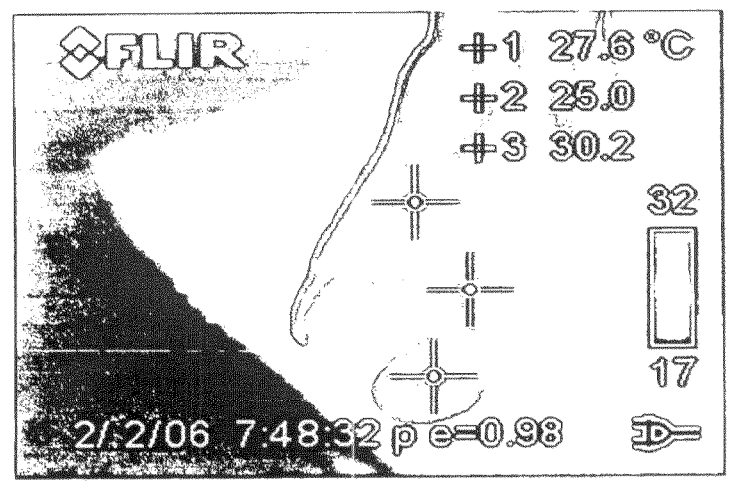

In the third thermograph provided in FIG. 7C, taken about 43 minutes after stimulation was initiated, instep point 3 has undergone a temperature rise of about 3C to 30.2C; the temperature of big toe base point 2 has risen to 25C, and big toe point 1 shows an appreciable temperature rise of about 7C to 27.6C. It is also evident from this thermograph image that all five toes have undergone warming.

Figure 7D:
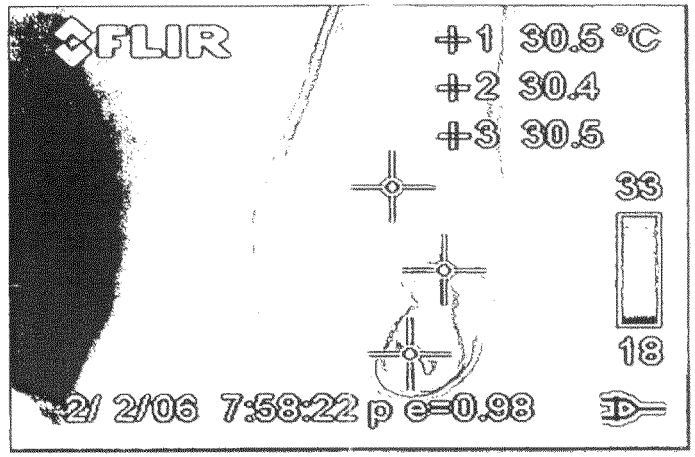
Figure 7E:
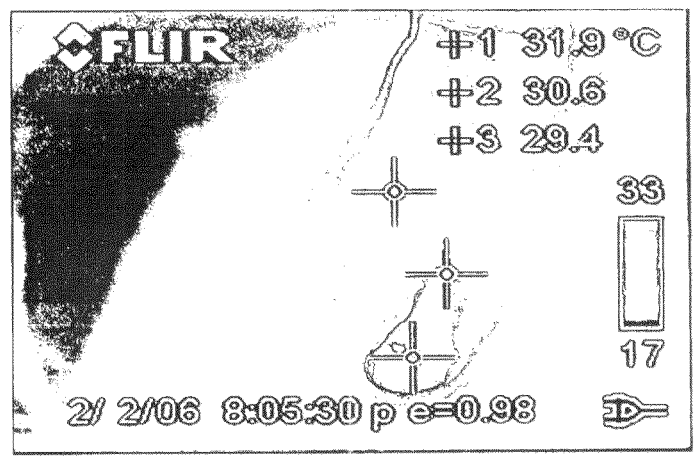

The fourth thermograph, provided in FIG. 7D, was taken about 53 minutes after stimulation was initiated. Instep point 3 is now at a temperature of 30.5C; the temperature of big toe base point 2 has rapidly risen to 30.4C, and big toe point 1 shows a temperature rise of another 3C to 30.5C. The other four toes also show signs of additional warming.

In the fifth thermograph (FIG. 7E), taken about one hour after stimulation was initiated, the measured points are similar to those of FIG. 7D. The four smaller toes continue to the warming trend.

Figure 7F:
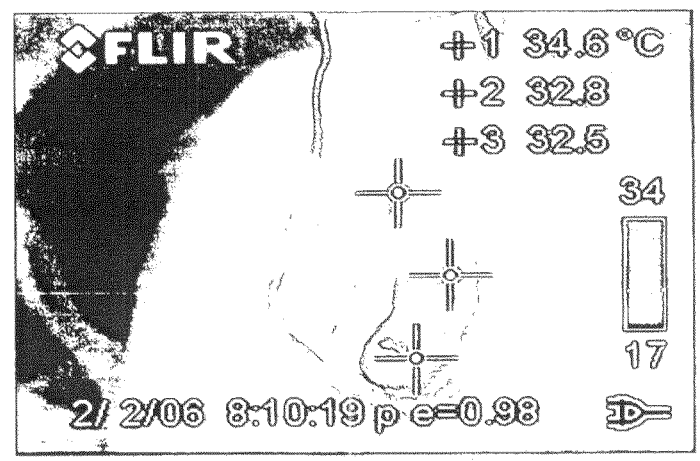

The final thermograph, provided in FIG. 7F, was taken about 65 minutes after stimulation was initiated. Instep point 3 is now at a temperature of 32.5C; the temperature of big toe base point 2 has risen to 32.8C, and big toe point 1 shows a temperature rise to 34.6C. The other four toes continue to warm up, such that the entire foot appears to be within the range of 30C-35C.

Figure 8:
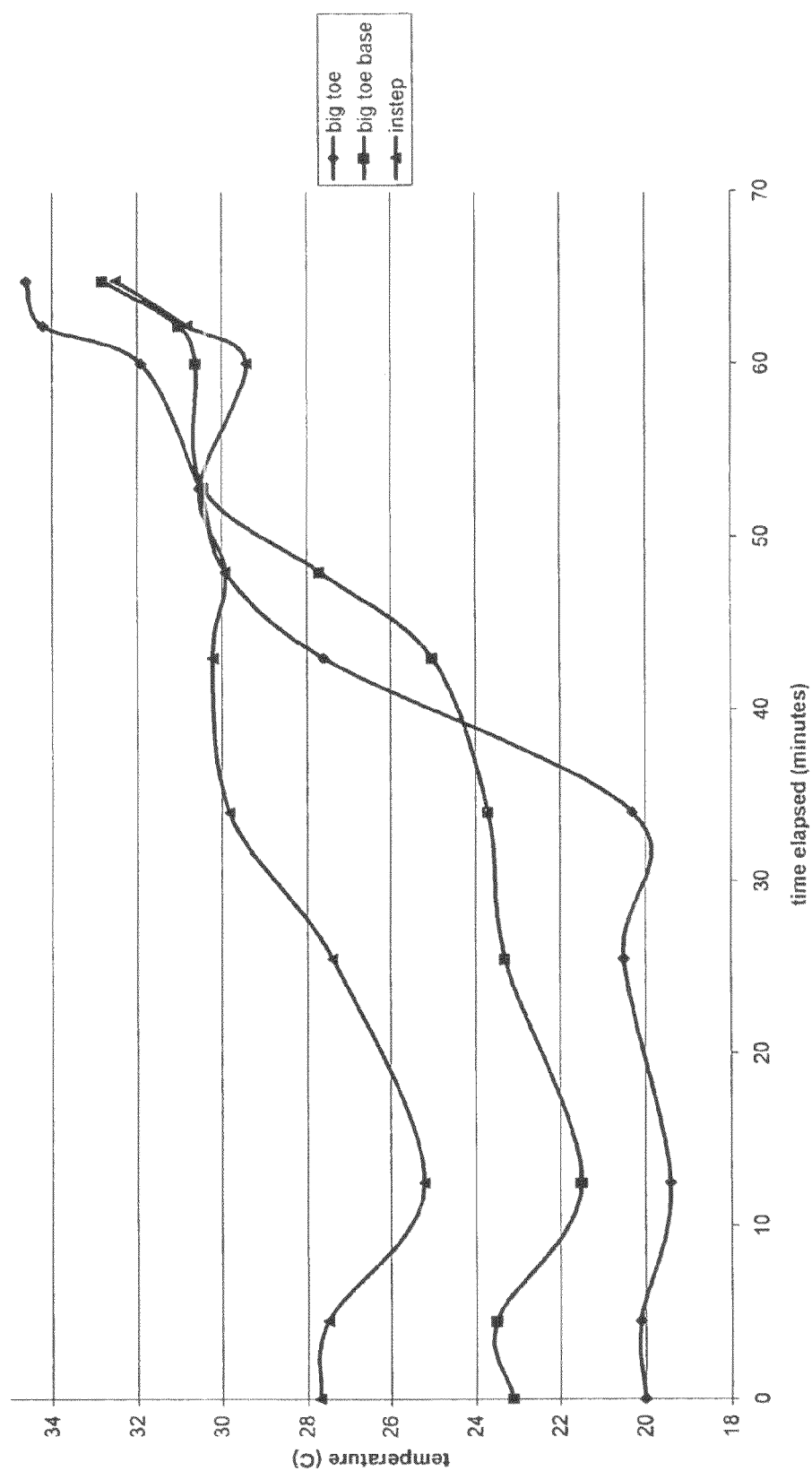
FIG. 8 is a plot of the temperature profile of three monitoring points on the foot, as a function of time, based, inter alia, on the thermographs of FIGS. 7A-7F.

The temperature profile of the three monitoring points, as a function of time, is provided in FIG. 8.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification, including U.S. Pat. Nos. 5,645,081, 6,458,109, and U.S. Patent Publication No. 20070270917, are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A non-invasive method for promoting a localized increase in a flow of blood through a blood vessel in a limb segment on a lower leg of a body of a subject, by a series of electrically stimulated contractions of muscle tissue in the limb segment, the method comprising the steps of: (a) providing a device including: (i) a plurality of electrodes including a first electrode, a second electrode, and a third electrode, each of said plurality of electrodes adapted to operatively contact the limb segment; (ii) a signal generator, operatively connected to each said electrode, adapted to produce a series of electrical impulses to the limb segment via said plurality of electrodes, said signal generator connecting to a power supply, and (iii) a control unit, associated with said signal generator, adapted to control said signal generator to produce said series of electrical impulses; (b) positioning said plurality of electrodes on the limb segment, wherein said first electrode is positioned on a lower end of the lower leg, said second electrode is positioned on the lower leg, and said third electrode is positioned on an upper end of the lower leg, whereby said first electrode and said third electrode are disposed on opposite ends of the lower leg, and said second electrode and one of said first and third electrodes are disposed on a same end of the lower leg; (c) effecting a sequence of muscular contractions of the lower leg, by operations including: (i) applying at least a first electrical impulse of said impulses between said electrodes on said same end of the lower leg to induce a first muscular contraction of a first portion of the tissue in the lower leg; and (ii) applying at least a second electrical impulse of said impulses between said first and third electrodes to induce a longitudinal muscular contraction of a second portion of the muscular tissue in the lower leg; and (d) repeating operations (i) and (ii), to repeatedly induce at least said first muscular contraction and said longitudinal muscular contraction, to effect the localized increase in the flow of blood.

2. The method of claim 1, wherein said plurality of electrodes includes a fourth electrode.

3. The method of claim 2, wherein said fourth electrode is positioned on an upper end of the lower leg.

4. The method of claim 2, wherein said sequence includes a muscular contraction of a third portion of the tissue in the lower leg, said contraction of said third portion of the tissue effected by applying at least one of said electrical impulses between said third electrode and said fourth electrode, positioned on the lower leg.

5. The method of claim 2, wherein said sequence of muscular contractions includes a second longitudinal contraction of a third portion of the tissue in the lower leg, said second longitudinal contraction of said third portion of the tissue effected by applying at least one of said electrical impulses between said fourth electrode and at least one electrode disposed on said lower end of the lower leg.

6. The method of claim 2, wherein said sequence of muscular contractions includes a second longitudinal contraction of a fourth portion of the tissue in the lower leg, said second longitudinal contraction of said fourth portion of the tissue effected by applying at least one of said electrical impulses between said fourth electrode and at least one electrode disposed on said lower end of the lower leg.

7. The method of claim 1, wherein said electrical impulses of said series of electrical impulses are time-distinct impulses.

8. The method of claim 1, wherein at least said first electrical impulse is applied in a radial direction with respect to the lower leg.

9. The method of claim 1, wherein said first electrode is positioned above an ankle of said leg.

10. The method of claim 1, wherein the lower leg has a particular length, and wherein said electrodes are positioned at opposite ends of the lower leg, whereby said longitudinal contraction is effected over substantially said particular length of the lower leg.

* * * * *